(12) United States Patent
Piedrahita et al.

(10) Patent No.: US 6,635,802 B1
(45) Date of Patent: Oct. 21, 2003

(54) NUCLEAR TRANSFER USING CELLS CULTURED IN SERUM STARVATION MEDIA CONTAINING APOPTOSIS INHIBITORS

(75) Inventors: Jorge A. Piedrahita, College Station, TX (US); Chang-Kyu Lee, Suwon (KR); Regina Weaks, Richardson, TX (US); Fuller Bazer, College Station, TX (US)

(73) Assignee: The Texas A&M University System, College Station, TX (US)

( * ) Notice: Subject to any disclaimer, the term of this patent is extended or adjusted under 35 U.S.C. 154(b) by 39 days.

(21) Appl. No.: 09/758,024

(22) Filed: Jan. 10, 2001

Related U.S. Application Data

(60) Provisional application No. 60/175,196, filed on Jan. 10, 2000.

(51) Int. Cl.[7] .............................. C12N 15/00; C12N 5/00
(52) U.S. Cl. ........................ 800/24; 435/375; 435/377; 435/384
(58) Field of Search ............................ 800/24; 435/325, 435/384, 375, 377

(56) References Cited

U.S. PATENT DOCUMENTS

| | | | |
|---|---|---|---|
| 5,258,367 A | 11/1993 | Bazer et al. | 514/6 |
| 5,453,357 A | 9/1995 | Hogan | 435/7.21 |
| 5,523,226 A | 6/1996 | Wheeler | 435/240.2 |
| 5,573,933 A | 11/1996 | Seamark et al. | 435/172.3 |
| 5,641,676 A | 6/1997 | Gough et al. | 435/325 |
| 5,670,372 A | 9/1997 | Hogan | 435/240.2 |
| 5,690,926 A | 11/1997 | Hogan | 424/93.1 |
| 5,945,577 A | * 8/1999 | Stice et al. | 800/24 |

FOREIGN PATENT DOCUMENTS

| | | |
|---|---|---|
| EP | 0774510 | 5/1997 |
| WO | WO 94/07997 | 4/1994 |
| WO | WO 95/10599 | 4/1995 |
| WO | WO 95/34636 | 12/1995 |
| WO | WO 97/07668 | * 3/1997 |
| WO | WO 97/07669 | * 3/1997 |
| WO | WO 97/47734 | 12/1997 |
| WO | WO98/07841 | 2/1998 |
| WO | WO 98/07841 | * 2/1998 |
| WO | WO 98/16630 | * 4/1998 |

OTHER PUBLICATIONS

Cibelli; Cloned Transgenic Calves Produced from Nonquiescent Fetal Fibroblasrs, 1998, Science, vol. 280: 1256–1258.*

Sims; Production of calves by transfer of nuclei from cultured inner cell mass cells, 1993, Proc. Natl. Acad. Sci., vol. 90: 6143–6147.*

Delhaise et.al.; Nuclear Transplantation using Bovine Primordial Germ Cells from Male Fetuses, 1995, Reproduc. Fertil. Dev. 7: 1217–1219.*

Shille; Animal Reproduction, 1999, Theriogenology, vol. 51: 1.*

Lee et.al.; Effects of Apoptosis Inhibitors on Survival of Porcine Primordial Germ Cells in Vitro, 1999, Theriogenology 51: 208.*

Simerly et al. Molecular Correlates of Primate Nuclear Transfer Failures. Science. Apr. 11, 2003, vol. 300, p. 297.*

Bondioli et al., "Production of identical bovine offspring by nuclear transfer," *Theriogenology*, 33:165, 1990.

Bondioli et al., "Production of transgenic cattle by pronuclear injection," *In: Transgenic Animals*, First and Haseltine (eds.), Butterwort–Heinnemann, MA, 265–273, 1991.

Campbell et al., "Sheep cloned by nuclear transfer from a cultured cell line," *Nature*, 380:64, 1996.

Castro–Obregon and Covarrubias, "Role of retinoic acid and oxidative stress in embryonic stem cell death and neuronal differentiation," *FEBS Letters*, 381:93–97, 1996.

Cherny and Merei, "Evidence for pluripotency of bovine primordial germ cell–derived cell lines maintained in long–term culture," *Theriogenology*, 41:175, 1994.

Cibelli et al., "Production of germline chimeric bovine fetuses from transgenic embryonic stem cells," *Theriogenology*, 46:241, 1997.

Delhaise et al., "Nuclear transplantation using bovine primoridial germ cells from male fetuses," *Reprod. Fertile. Dev.*, 7:1217–1219, 1995.

Evans et al., "Derivation and preliminary characterization of pluripotent cell lines from porcine and bovine blastocysts," *Theriogenology*, 33:125–128, 1990.

Evans and Kaufman, "Pluripotential cells grow directly from normal mouse embryos," *Cancer Surveys*, 2:185–207, 1983.

Gerfen and Wheeler, "Isolation of embryonic cell–lines from porcine blastocysts," *Anim. Biotech*, 6:1–14, 1995.

Handyside et al., "Towards the isolation of embryonal stem cell lines from the sheep," *Roux's Arch. Dev. Biol.*, 196:185–190, 1987.

Lavoir et al., "Development of bovine nuclear transfer embryos made with oogonia," *Biol. Reprod.*, 56:194–199, 1997.

Lavoir et al., "Isolation and identification of germ cells from fetal bovine ovaries," *Molecular Reproduction and Development*, 37:413–424, 1994.

Lee et al., "Effects of protease inhibitors and antioxidants on survival of porcine primoridal gem cells in vitro," *Biol. Reprod.*, 63(3):887–897, 2000.

(List continued on next page.)

Primary Examiner—Deborah Crouch
(74) Attorney, Agent, or Firm—Bracewell & Patterson LLP

(57) ABSTRACT

Provided are methods and compositions for increasing the efficiency of nuclear transfer using apoptosis inhibitors, and for the production of transgenic and non-transgenic mammals from cultured cells or cell lines. Methods for cloning mammals, and for producing transgenic and chimeric mammalian tissues and mammals, and chimeric cell lines are also provided.

60 Claims, 5 Drawing Sheets

OTHER PUBLICATIONS

Lee et al., "Effects of apoptosis inhibitors on survival of porcine primordial germ cells in vitro," *Theriogenology*, 51:208, 1999.

Leichthammer and Brem, "In vitro culture and cryopreservation of farm animals' primordial gem cells," *Theriogenology*, 33:272, 1990.

Liu et al., "Nuclear remodeling and early development in cryopreserved, porcine primordial germ cells following nuclear transfer into in vitro–matured oocytes," *Int. J. Dev. Biol.*, 39:639–644, 1995.

Lo et al., "Expression of mouse IgA by transgenic mice, pigs and sheep," *Eur. J. Immunol.*, 21:1001–1006, 1991.

Lotem et al., "Cellular oxidative stress and the control of apoptosis by wild–type p53, cytotoxic compounds, and cytokines," *Proc. Natl. Acad. Sci. USA*, 93:9166–9171, 1996.

Moens et al., "Assessment of nuclear totipotency of fetal bovine diploid germ cells by nuclear transfer," *Theriogenology*, 46:871–880, 1996.

Moore and Piedrahita, "Effects of heterologous hematopoietic cytokines on in vitro differentiation of cultured porcine inner cell masses," *Mol. Reprod. Dev.*, 45:139–144, 1996.

Moore and Piedrahita, "The effects of human leukemia inhibitory factor (HLIF) and culture medium on in vitro differentiation of cultured porcine inner cell mass (PICM)," *In vitro Cell Dev. Biol.—Animal*, 33:62–71, 1997.

Moreno and Westhusin, "A Comparison of two systems for culture of bovine zygotesin in vitro," *Biol. Reprod.*, 48(1):169, 1993.

Notarianni et al., "Derivation of pluripotent, embryonic cell lines from pig and sheep," *J. Reprod. Fertil.*, 43(suppl.):255, 1991.

Notarianni et al., "Maintenance and differentiation in culture of pluripotential embryonic cell lines from pig blastocysts," *J. Reprod. Fertil.*, 41(suppl):51–56, 1990.

Ohta et al., "Requirement of the Caspase–3/CPP32 Protease cascade for apoptotic death following cytokine deprivation in hematopoietic cells," *J. Biol. Chem.*, 272(37):23111–23116, 1997.

Onishi et al., "Production of chimeric pigs and the analysis of chimerism using mitochondrial deoxyribonucleic acid as a cell marker," *Biol. Reprod.*, 51:1069–1075, 1994.

Pesce and De Felici, "Apoptosis in mouse primordial germ cells: a study by transmission and scanning electron microscope," *Anat. Embryol.*, 189:435–440, 1994.

Pesce et al., "Stem cell factor and leukemia inhibitory factor promote primordial germ cell survival by suppressing programmed cell death (apoptosis)," *Development*, 118:1089–1094, 1993.

Petters and Wells, "Culture of pig embryos," *J. Reprod. Fert. Suppl.*, 48:61–73, 1993.

Piedrahita et al., "Influence of feeder layer type on the efficiency of isolation of porcine embryo–derived cell lines," *Theriogenology*, 34(5):865–877, 1990.

Piedrahita et al., "On the isolation of embryonic stem (ES) cells: Comparative behavior of murine, procaine, and ovine embryos," *Theriogenology*, 34:879–901, 1990.

Prather et al., "Nuclear transplantation in pig embryos," *Biol. Reprod.*, 41:414–418, 1989.

Saito et al., "Bovine embryonic stem cell–like cell lines cultured over several passages," *Roux's Arch. Dev. Biol.*, 201:134–141, 1992.

Shim et al., "Isolation of pluripotent stem cells from cultured porcine primordial germ cells," *Theriogenology*, 46:245, 1997.

Shim and Anderson, "Putative porcine embryonic germ cells maintained in long–term culture," *Society for the Study of Reproduction, Biology of Reproduction*, 28th Annual Meeting, University of California, vol. 52/Supplement 1:317–320, Abstract 320, Jul. 9–12, 1995.

Stefanis et al., "Inhibitors of trypsin–like serine proteases inhibit processing of the caspase Nedd–2 and protect PC12 cells and sympathetic neurons from death evoked by withdrawal of trophic support," *J. Neurochem.*, 69(4):1425–1437, 1997.

Stewart et al., "Stem cells from primordial germ cells can reenter the germline," *Dev. Biol.*, 161:626–628, 1994.

Stice et al., "Pluripotent bovine embryonic cell lines direct embryonic development following nuclear transfer," *Biol. Reprod.*, 54:100–110, 1996.

Stice et al., "Bovine pluripotent embryonic cells contribute to nuclear transfer and chimeric fetuses," *Theriogenology*, 41:301 (Abstract), 1994.

Stokes et al., "Production of chimaeric bovine embryos," *Theriogenology*, 41:303–309, 1994.

Strelchenko, "Bovine pluripotent stem cells," *Theriogenology*, 45:131–140, 1996.

Strojek et al., "A method for cultivating morphologically undifferentiated embryonic stem cells from porcine blastocysts," *Theriogenology*, 33:901, 1990.

Sukoyan et al., "Embryonic stem cells derived from morulae, inner cell mass, and blastocyst of mink: comparisons of their pluripotencies," *Mol. Reprod. Dev.*, 36:148, 1993.

Tewari and Dixit, "Fas– and tumor necrosis factor–induced apoptosis is inhibited by the poxvirus crmA gene product," *J. Biol. Chem.*, 270(7):3255–3260, 1995.

Tilly and Tilly, "Inhibitors of oxidative stress mimic the ability of follicle–stimulating hormone to suppress apoptosis in cultured rat ovarian follicles," *Endocrinology*, 136:242–252, 1995.

Wheeler, "Development and validation of swine embryonic stem cells—A review," *Reprod. Fertil. Dev.*, 6:563–570, 2994.

Wheeler et al., "Production of chimeric swine from embryonic stem (ES) cells," *Society for the Study of Reproduction, Biology of Reproduction*, 28th Annual Meeting, University of California, vol. 52/Supplement 1:317–320, Abstract 319, Jul. 9–12, 1995.

Wilmut et al., "Viable offspring derived from fetal and adult mammalian," *Nature*, 385:810–813, 1997.

\* cited by examiner

US 6,635,802 B1

NUCLEAR TRANSFER USING CELLS CULTURED IN SERUM STARVATION MEDIA CONTAINING APOPTOSIS INHIBITORS

The present application claims priority to provisional application Ser. No. 60/175,196, filed Jan. 10, 2000, the entire text and figures of which application is incorporated herein by reference without disclaimer. Applicants reserve the right to claim priority to U.S. application Ser. No. 08/949,155, filed Oct. 10, 1997, now U.S. Pat. No. 6,271,436 which is also incorporated herein by reference without disclaimer irrespective of the potential claim for priority.

The U.S. government owns rights in the present invention pursuant to grant number HL51587 from the National Institutes of Health.

BACKGROUND OF THE INVENTION

1. Field of the Invention

The present invention relates generally to the field of mammalian cell biology. More particularly, it concerns methods and compositions using apoptosis inhibitors to increase the efficiency of nuclear transfer, useful in the production of transgenic and non-transgenic mammals from cultured cells or cell lines. Methods using apoptosis inhibitors in cloning mammals, and for producing chimeric cell lines, transgenic and chimeric mammalian tissues and mammals are also provided.

2. Description of Related Art

The basic procedure for nuclear transfer concerns obtaining single cells and fusing them to enucleated recipient ovum. This effectively transfers the nucleus of the donor cell into the recipient cytoplasm where, if successful, it is reprogrammed and subsequently instructs development of a new embryo that is genetically identical to that from which the cell was acquired. Nuclei from embryonic fibroblasts as well as adult mammary epithelial cells can direct normal development in the sheep (Wilmut et al., 1997).

Although the nuclear transfer technique is less advanced in pigs, there have been reports of successful births using nuclei from 4-cell embryos (Prather et al., 1989). Primordial germ cells (PGCs) collected from fetal tissue have also been successfully utilized as donors for nuclear transplantation (Cherny and Merei, 1994, Delhaise et al., 1995, Lavoir et al., 1997, Strelchenko, 1996). In pigs it has been demonstrated that previously cryopreserved PGCs can be used successfully as nuclear donors, giving rise to nuclear reprogramming and cleavage to the 4-cell stage (Liu et al., 1995). Additionally, nuclear reprogramming in cultured ICM-derived pig cells after nuclear transfer has been reported (Ouhibi et al., 1996). The ability of the embryos to participate in normal development was not studied.

In a recent study in cattle, 9–13% of cleaved nuclear transplant embryos developed to the blastocyst stage when oogonia collected from female fetuses (50–70 days gestation) was utilized as nuclei donors (Lavoir et al., 1997). Although no live calves were produced, an abnormal conceptus developed in one animal that had received 4 embryos. This conceptus was recovered by induced abortion at day 43 after failing to detect a heartbeat, and genetic analysis showed the fetus to be genetically identical to the donor oogonia. Similar results using bovine PGCs from both male and female fetuses have been reported (Moens et al., 1996). The observation that nuclei from cultured bovine PGCs can direct development up to day 60 with no significant fetal abnormalities reported suggests that, when PGCs are placed in culture, nuclear changes occur that increase the nuclear potency of the cells when compared with freshly isolated PGCs (Strelchenko, 1996).

In spite of the foregoing reports, the technique of nuclear transfer is plagued by extremely low efficiency. Thus, methods and compositions that increase the efficiency of nuclear transfer, using both cultured somatic and germ cells, would represent a significant advance in the art.

SUMMARY OF THE INVENTION

The present invention overcomes one or more of the shortcomings in the art by providing methods and compositions using apoptosis inhibitors to increase the number of cells available for manipulation, including homologous recombination and gene targeting, in the generation of cell lines, transgenic and chimeric tissues and animals. The methods and compositions of the invention increase the efficiency of nuclear transfer, for use in the production of transgenic and non-transgenic mammals from cultured cells or cell lines, in cloning mammals, and for producing chimeric cell lines, transgenic and chimeric mammalian tissues and mammals.

The present invention thus provides methods and compositions for increasing, and preferably significantly increasing, the number and/or proportion of nuclear transfer-competent cells within a mammalian cell population. These methods and compositions comprise contacting, providing, administering, admixing or culturing a mammalian cell population with an amount of at least a first apoptosis inhibitor effective to increase, and preferably significantly increase, the number and/or proportion of nuclear transfer competent cells within the mammalian cell population.

The invention further provides methods and compositions for performing nuclear transfer in which the efficiency of nuclear transfer is increased, and preferably, significantly increased. Such methods and compositions comprise maintaining or culturing a mammalian cell population in the presence of an amount of at least a first apoptosis inhibitor effective to increase, and preferably significantly increase, the number and/or proportion of nuclear transfer competent cells within the cell population and fusing at least a first nuclear transfer-competent cell therefrom with a suitable enucleated, recipient cell or ovum.

A "nuclear transfer-competent cell", as used herein, means a cell capable of being used in conjunction with a suitable enucleated, recipient cell in an effective nuclear transfer method. The present invention therefore provides methods and compositions for increasing, and preferably significantly increasing, the number and/or proportion of nuclear transfer-competent cells from within mammalian cell populations contemplated for use in nuclear transfer.

"Nuclear transfer-competent cells" are preferably in the G0/G1 stage of the cell cycle and, as used herein, are "viable" in the sense that they are capable of effectively participating in nuclear transfer in conjunction with suitable enucleated, recipient cell(s) to produce functional nucleated cells, reprogrammed nucleated cells, and reprogrammed nucleated cells capable of instructing the development of a new embryo. The invention thus provides methods and compositions for increasing, and preferably significantly increasing, the number and/or proportion of viable, nuclear transfer-competent cells (nuclear transfer-compeient, viable cells) from within cell populations contemplated for use in nuclear transfer.

In such methods and compositions of the invention, it is the contact, provision, administration, admixture or culture of the cell population comprising the cells for use in nuclear transfer in the presence of an effective amount of at least a first apoptosis inhibitor that increases or significantly increases the number and/or proportion of viable, nuclear transfer-competent cells.

To complete the nuclear transfer process, the viable, nuclear transfer-competent cell or cells is/are fused with suitable enucleated, recipient cell(s), thereby achieving nuclear transfer, i.e., transfer of the donor nucleus into the enucleated cell to produce a viable, nucleated cell, reprogrammed nucleated cell and/or reprogrammed, nucleated cell capable of instructing the development of a new embryo.

Accordingly, the invention provides increasingly effective and efficient methods and compositions for performing nuclear transfer. Such methods and compositions comprise culturing or maintaining a mammalian cell population containing at least some cells or a sub-population of cells at the G0/G1 stage of the cell cycle in media comprising an effective amount of at least a first apoptosis inhibitor, thereby increasing the number and/or proportion of viable cells within the G0/G1 stage cells of said cell population; and fusing at least a first viable G0/G1 cell with an enucleated mammalian ovum. The "effective amount" of the at least a first apoptosis inhibitor is an amount effective to increase the number and/or proportion of viable G0/G1 cells in the G0/G1 sub-population or overall cell population.

In the methods and compositions for performing nuclear transfer of the invention, the "mammalian cell population" is "at least a first mammalian cell population", which at least a first mammalian cell population comprises at least one, some or a sub-population of cells at the G0/G1 stage of the cell cycle. Culture or maintenance with an effective amount of at least a first apoptosis inhibitor thereby increases the number and/or proportion of viable cells within the G0/G1 cells of said sub-population or said overall cell population.

In certain embodiments, the invention provides methods of performing nuclear transfer that comprise culturing at least a first mammalian cell in serum starvation media comprising at least a first apoptosis inhibitor for a period of time effective to arrest the at least a first cell at the G0/G1 stage of the cell cycle, and fusing the cell cycle arrested cell with an enucleated mammalian ovum.

Any method may be employed to initially obtain a mammalian cell population comprising potentially nuclear transfer competent cells, preferably a mammalian cell population comprising potentially viable G0/G1 cells, such that execution of the invention increases the actual nuclear transfer competent cells or actual viable G0/G1 cells within the cell population. Suitable methods that induce cells within a cell population to enter the G0/G1 stage of the cell cycle include those involving chemical treatment, nutrient deprivation, growth inhibition, manipulation of gene expression or combinations thereof. A preferred method of the invention is to culture the cell population in serum starvation media.

In the methods and compositions of the invention, it is the contact, provision, administration, admixture or culture of the cell population in the presence of an effective amount of at least a first apoptosis inhibitor that increases or significantly increases the number and/or proportion of viable, nuclear transfer-competent cells. The "effective amount" of at least a first apoptosis inhibitor refers to both an effective mass and concentration, and to an effective period of time that the cell population is exposed to the apoptosis inhibitor.

The interplay of the "effective amounts and times" will be known those of ordinary skill in the art in light of the present disclosure. By way of example, it will be understood that, within the teachings of the present disclosure, "effective" contact with apoptosis inhibitors overall can be achieved using a lower amount or concentration for a longer time, or a higher amount or concentration for a shorter time.

To the extent that, in certain aspects of the present invention, there may be an "interdependence" of time and dosage, the determination of "effective amounts" is still within the level of skill in the art in light of the present disclosure. For example, in reference to Example I, the ordinary skilled artisan will understand that the use of MAC is preferred at mid-levels of the disclosed ranges, whereas NAC is preferred at high levels of the disclosed ranges and above. The ordinary skilled artisan will also understand that maximal effects result when MAC is present substantially throughout the culture or "incubation period" of the cell population, whereas NAC need only be present at, substantially at, or at a time proximal to, the initial stages of the culture or incubation to have its most beneficial effect.

In certain embodiments, the mammalian cell population will contain somatic or germ cells from a mammal, whether immature or adult, a fetus or an embryo, such that the invention provides viable somatic or germ cells from a mammal in G0/G1. Preferred somatic cells include, but are not limited to, mammary gland cells and granulosa cells. Preferred germ cells include, but are not limited to, primordial germ cells (PGCs), fetal lung fibroblast cells and embryonic fibroblast cells, for example bovine or porcine embryonic fibroblast cells. The methods and compositions of the present invention may be used in conjunction with those of co-owned, co-pending U.S. application Ser. No. 08/949,155, filed Oct. 10, 1997, specifically incorporated herein by reference.

Accordingly, as disclosed in U.S. application Ser. No. 08/949,155, incorporated herein by reference, the present invention further pertains to methods of growing or culturing cells, preferably fetal or embryonic fibroblasts or primordial germ cells, comprising growing a cell culture or population comprising the cells of interest, preferably fetal or embryonic fibroblasts or primordial germ cells, on an effective density of feeder cells and in a biologically effective culture medium comprising an amount of at least a first apoptosis inhibitor effective to increase the number of nuclear transfer competent cells when said cell culture or population is grown, cultured or maintained under conditions and for a time sufficient to obtain undifferentiated cells, preferably undifferentiated fetal or embryonic fibroblasts or primordial germ cells, including nuclear transfer competent cells. The use of bovine and porcine cells in such methods is currently preferred.

U.S. application Ser. No. 08/949,155, incorporated herein by reference, exemplifies various effective feeder cells and effective densities thereof, as well as various biologically effective culture media. All such feeder cells, media components and concentrations may be used in the present invention. The cells and media in U.S. application Ser. No. 08/949,155 are exemplary only, any many such feeder cells, densities and biologically effective culture media are known and can be used in conjunction with the present invention.

The methods and compositions of the invention include those wherein the cell population comprises viable G0/G1 cells that comprise at least a first exogenous DNA segment. In that the present invention increases the efficiency of homologous recombination, gene targeting and nuclear transfer, viable G0/G1 cells that comprise at least a first exogenous DNA segment, and resultant cells, cell lines, blastocysts, oocytes, embryos and animals, are advantageous aspects of the invention.

As disclosed in U.S. application Ser. No. 08/949,155, incorporated herein by reference, the variety of exogenous DNA segments that may be included with the present invention is virtually limitless. The selected DNA segment may comprise at least a first coding region encoding a selected protein. However, protein production is not a requirement of the invention, which may be effectively practiced, e.g., using antisense or ribozyme technology, wherein the expression of an RNA species provides a desired phenoty sult. Where protein expression is desired, an exogenous coding region may encode a selected marker protein, such as green fluorescent protein (GFP).

In important embodiments, an exogenous coding region will be supplied that encodes an RNA or protein with a desired biological activity, including proteins that are physiologically or pharmacologically active (or rendered physiologically or pharmacologically active upon expression). In preferred embodiments, the encoded protein confers disease resistance, carcass composition, weight gain, coat composition or is a milk component protein.

An encoded RNA or protein may be physiologically or pharmacologically active only in specific tissues or may be active in a variety of sites or tissues. Proteins that are converted to an active form in an animal, e.g., through the action of enzyme-assisted transformation, pH, specific organ activities, and such like, or through the application of at least one more exogenous agent(s) are included. Proteins may also be adapted to increase expression in the chosen animal, e.g., by altering the coding sequence of the protein to use codons that are preferred for use in the particular animal.

Suitable examples of encoded products for use with the present invention include transcription or elongation factors, cell cycle control proteins, enzymes, kinases, phosphatases, DNA repair proteins, oncogenes, tumor suppressors, cytotoxins, angiogenic proteins, anti-angiogenic proteins, apoptosis-inducing agents, anti-apoptosis agents, immune system proteins, antigens, immune response stimulating proteins, cell surface receptors, accessory signaling molecules, transport proteins, enzymes, anti-bacterial, anti-microbial, anti-parasitic or anti-viral proteins or polypeptides.

Further suitable examples include hormones, neurotransmitters, growth factors, growth factor receptors, hormone receptors, neurotransmitter receptors, adhesion ligands, binding proteins, interferons, interleukins, chemokines, cytokines, colony stimulating factors and chemotactic factor proteins. Yet further examples are extracellular matrix components, molecules, ligands and peptides, such as collagens, fibrin, fibronectin, vitronectin, hyaluronic acid, RGD-containing peptides or polypeptides. Even further examples are blood proteins and muscle proteins and components.

Certain particular examples, as disclosed in U.S. application Ser. No. 08/949,155, specifically incorporated herein by reference, are SREHP, GP63, actinobacillus, pleuropneumoniae, pseudomonas aeruynosa, OprF, myelin basic protein, insulin, hCD59, DAF (CD55), factor IX, urokinase, α-antitrypsin, tissue plasminogen activator, protein C, activin, adenosine deaminase, angiotensinogen I, antithrombin III, alpha I antitrypsin, apolipoprotein A-I, apolipoprotein A-II, apolipoprotein C-I, apolipoprotein C-II, apolipoprotein C-III, apolipoprotein E, atrial natriuretic factor, chorionic gonadotropin, alpha chain, beta chain, pro (rennin) chymosin, factor B complement, complement C2, complement C3, complement C4, complement C9, corticotropin releasing factor, epidermal growth factor, c-erb B, epoxide dehydratase, erythropoietin, C1 esterase inhibitor, factor VIII, factor IX, Christmas factor, factor X, fibrinogen A alpha, gamma B beta, gastrin releasing peptide, prepro glucagon, growth hormone, RF growth hormone, somatocrinin, hemopexin, inhibin, prepro insulin, insulin-like growth factor I, insulin-like growth factor II, alpha interferon, multiple leukocyte, fibroblast beta interferon, gamma interferon, interleukin-1, T-cell interleukin-2, growth factor, interleukin-3, two forms kininogen, beta subunit leuteinizing hormone, leuteinizing hormone, releasing hormone, lymphotoxin, mast cell growth factor, beta subunit nerve growth factor, PGDF c-sis oncogene, chain A, pancreatic polypeptide, icosapeptide, parathyroid hormone, prepro plasminogen, plasminogen activator, prolactin, proopiomelanocortin, protein C, prothrombin, relaxin, prepro renin, somatostatin, prepro tachykinin, substance P, substance K, urokinase and prepro vasoactive intestinal peptide protein.

Particular preferably proteins are GP63, myelin basic protein, hCD59, Factor IX, α-antitrypsin, α-casein, interleukins and Bcl-2.

The viable G0/G1 cells of the invention may further comprise one or two exogenous DNA segments, wherein the one or two exogenous DNA segments comprise at least a first and second coding region that each express a selected protein. Certain advantages are wherein the first coding region encodes a physiologically or pharmacologically active protein or RNA and the second coding region encodes a selected marker protein. In certain embodiments, such coding regions are preferably on the same exogenous DNA segment.

The exogenous DNA segment(s) may be operatively positioned under the control of an exogenous promoter that directed expression in the chosen cell type, although the use of an exogenous promoter is not necessary to the practice of the invention. The selected DNA segment(s) may be introduced into the cells by any suitable method, such as, e.g., by electroporation, particle bombardment, viral transformation or such like.

In certain preferred embodiments, the exogenous DNA segment further comprises two selected DNA regions that flank the DNA segment, thereby directing the homologous recombination of the DNA segment into the genomic DNA of the target cells, i.e., the viable G0/G1 cells. In such embodiments, the DNA segment may further comprise two selected DNA sequences that flank the DNA segment, thereby directing excision of the DNA segment under appropriate conditions. Examples of such selected DNA sequences are loxP sites, for use with the Cre Lox system. Such homologous recombination techniques are disclosed in U.S. application Ser. No. 08/949,155, incorporated herein by reference.

Also as disclosed in U.S. application Ser. No. 08/949,155, incorporated herein by reference, this invention therefore concerns methods of preparing mammalian cells at the G0/G1 stage of the cell cycle that contain a selected DNA segment, comprising (a) culturing a mammalian cell population containing cells at the G0/G1 stage of the cell cycle in media comprising an amount of at least a first apoptosis inhibitor effective to increase the proportion of viable G0/G1 cells in the cell population; and (b) introducing a selected DNA segment into the viable G0/G1 cells in said cell population.

The present invention is applicable to all animals, particularly valuable or valued animals, such as farm animals used to produce food for human consumption and breeding stock, race horses, domestic pets, zoological animals and research animals. In addition, for aspects concerning the generation of cells, not whole animals, the present invention applies to producing human cells, e.g., for culture and/or use in human treatment. Thus, "transgenic and cloned whole mammals" exclude humans.

In particular aspects of the invention, the mammalian cell populations therefore contain cells from a lagomorph (gnawing, herbivorous mammal, e.g., rabbit), bovine (cow), porcine (pig,), ovine (sheep), equine (horse), caprine (goat), canine (dog), feline (cat), murine (mouse), non-human primate (monkey, chimpanzee, etc.) or human primate species. Cells from boar, buffalo, bison, llama, deer, elk, lion, tiger, zebra, giraffe, elephant, panda, and other large animals, as well as their young, are also included. As nuclear transfer technology has been applied outside the field of mammals, cells from non-mammals, such as birds, amphibians and fish are included, particularly commercially relevant birds, such as chicken, turkey, duck, goose, ostrich, emus, dove, quail, and the like.

In certain embodiments, the apoptosis inhibitors for use in the invention will be one or more serine protease-type apoptosis inhibitors ("serine protease inhibitors") or antioxidant-type apoptosis inhibitors ("antioxidants"). Preferred serine protease inhibitors include, but are not limited to, α2-macroglobulin (MAC), uteroferrin rose, 4-(2-aminoethyl) benzenesulfonyl hydrochloride (AEBSF), N-alpha-p-tosyl-L-lysine chloromethyl ketone (TLCK), 3,4-dichloroisocoumarin, serpins and E64 class serine protease inhibitors. MAC, AEBSF and TLCK are currently preferred. MAC is particularly preferred, with concentrations of between about 0.3 and about 1.50 pM MAC being more preferred, and about 0.7 pM MAC being particularly preferred.

Preferred antioxidants include, but are not limited to, N-acetylcysteine (NAC), butylated hydroxyanisole (BHA), cimetidine (CIM), N-t-butyl-α-phenylnitrone (BPN), thioredoxin and glutathione (GSH). NAC, BHA, BPN, CIM and GSH are preferred, particularly at concentrations about those listed in Table 7 or about 2.0 mM for GSH. NAC is one such preferred agent, with concentrations of between about 0.2 and about 3.0 mM or more NAC being preferred, such as at least about 2.0 mM NAC or about 2.0 mM NAC being particularly preferred.

In certain preferred embodiments of the invention, at least a first and second apoptosis inhibitor is used. For example, distinct serine protease inhibitors, distinct antioxidants, or combinations of serine protease inhibitors and antioxidants, such as combinations of α2-macroglobulin and N-acetylcysteine. In further aspects of the invention, three, four, five, six, or more, such as a plurality of apoptosis inhibitors, are used.

In that the cell populations of the invention need to be cultured, a convenient method of obtaining a starting cell population of mammalian cells comprising potentially nuclear transfer competent cells, such as potentially viable G0/G1 cells, is to culture the cell population in serum starvation media. Accordingly, the serum starvation media will preferably contain the at least a first apoptosis inhibitor for use in the invention.

In certain embodiments, the serum starvation media will comprise between about 0.05% and about 2% serum. It will be understood that all sub-ranges are included within this range, such as between about 0.1% and about 2%, between about 0.25% and about 2%, between about 0.5% and about 2%, between about 1% and about 2%, between about 1.5% and about 2%, between about 0.05% and about 1.5%, between about 0.05% and about 1%, between about 0.05% and about 0.5%, between about 0.05% and about 0.25%, between about 0.05% and about 0.1%, between about 0.1% and about 1.5%, between about 0.25% and about 1% and between about 0.5% and about 0.75% and such like. In preferred embodiments, the serum starvation media comprises between about 0.1% and about 0.5% serum. In other aspects, the serum starvation media comprises about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1%, about 1.1%, about 1.2%, about 1.25%, about 1.3%, about 1.4%, about 1.5 %, about 1.6%, about 1.7%, about 1.75%, about 1.8% or about 1.9% serum and such like.

In certain aspects of the invention, the nuclear transfer competent or viable G0/G1 cell(s) and the enucleated recipient cell or ovum are from the same mammalian species, while in other aspects, the nuclear transfer competent or viable G0/G1 cell(s) and the enucleated recipient cell or ovum are from distinct mammalian species, for example a human cell and a bovine enucleated ovum, for the generation of tissues for transplantation into humans. In preferred aspects of the invention, the nuclear transfer competent or viable G0/G1 cell(s) and the enucleated recipient cell or ovum are from a lagomorph, bovine, porcine, ovine, equine, caprine, canine, feline, murine, non-human primate, or human primate species. Cells from boar, buffalo, bison, llama, deer, elk, lion, tiger, zebra, giraffe, elephant, panda, and other large animals, as well as their young, are also included.

In further aspects of the invention, a population of mammalian cells is cultured and a single viable G0/G1 cell from the population is fused with the enucleated mammalian ovum. Irrespective of the number of cells for fusion, the cells may be cultured under the conditions of the invention for between about 3 and about 30 days; preferably, for between about 5 and about 14 days; and more preferably, for about 10 days or so. With any and all intermediate and partial ranges being included, such as 2.5, 3, 3.5, 4, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, and the like.

An exemplary method of the invention comprises culturing a cell population containing bovine or porcine fetal or embryonic fibroblasts or primordial germ cells at the G0/G1 stage of the cell cycle in serum starvation media comprising an amount of at least a first apoptosis inhibitor effective to increase the proportion of viable G0/G1 cells in the cell population; and fusing at least a first viable G0/G1 cell from the cultured cell population with an enucleated bovine or porcine ovum, thereby achieving nuclear transfer. Preferably, the apoptosis inhibitor is a MAC, NAC, BHA, CIM, BPN or GSH apoptosis inhibitor, and more preferably, the media comprises at least a first serine protease apoptosis inhibitor and at least a second antioxidant apoptosis inhibitor.

Another exemplary method of the invention comprises culturing a mammalian cell population, preferably a bovine or porcine fetal or embryonic fibroblast or primordial germ cell population, containing cells at the G0/G1 stage of the cell cycle in serum starvation media comprising an amount of the apoptosis inhibitor α2-macroglobulin (MAC) effective to increase the proportion of viable G0/G1 cells in the cell population when present substantially throughout the culture of said cell population; and fusing at least a first viable G0/G1 cell from the cultured cell population with an enucleated mammalian ovum, thereby achieving nuclear transfer.

A still further exemplary method of the invention comprises culturing a mammalian cell population, preferably a bovine or porcine fetal or embryonic fibroblast or primordial germ cell population, containing cells at the G0/G1 stage of the cell cycle in serum starvation media comprising an apoptosis inhibitor selected from the group consisting of N-acetylcysteine (NAC), butylated hydroxyanisole (BHA), cimetidine (CIM), N-t-butyl-α-phenylnitrone (BPN) and glutathione (GSH) in an amount effective to increase the proportion of viable G0/G1 cells in the cell population; and fusing at least a first viable G0/G1 cell from the cultured cell population with an enucleated mammalian ovum, thereby achieving nuclear transfer.

A yet further exemplary method of the invention comprises culturing a mammalian cell population, preferably a bovine or porcine fetal or embryonic fibroblast or primordial germ cell population, containing cells at the G0G1 stage of the cell cycle in serum starvation media comprising an amount of the apoptosis inhibitor N-acetylcysteine (NAC) effective to increase the proportion of viable G0/G1 cells in the cell population when present at the initial stages of the culture of said cell population; and fusing at least a first viable G0/G1 cell from the cultured cell population with an enucleated mammalian ovum, thereby achieving nuclear transfer.

Yet another exemplary method of the invention comprises culturing a mammalian cell population, preferably a bovine or porcine fetal or embryonic fibroblast or primordial germ cell population, containing cells at the G0/G1 stage of the cell cycle in serum starvation media comprising at least a first serine protease apoptosis inhibitor and at least a second antioxidant apoptosis inhibitor in a combined effective to increase the proportion of viable G0/G1 cells in the cell population; and fusing at least a first viable G0/G1 cell from the cultured cell population with an enucleated bovine or porcine ovum, thereby achieving nuclear transfer.

In certain embodiments, the use of α2-macroglobulin is excluded from the invention, so that the invention concerns methods of nuclear transfer, and associated methods and compositions, all of which comprise culturing a mammalian cell population containing cells at the G0/G1 stage of the cell cycle in media comprising at least a first serine protease apoptosis inhibitor other than α2-macroglobulin in an amount effective to increase the proportion of viable G0/G1 cells in the cell population; and fusing at least a first viable G0/G1 cell with an enucleated mammalian ovum.

In certain other embodiments, the use of the antioxidant apoptosis inhibitor thioredoxin is specifically excluded from the invention, so that the invention concerns methods of nuclear transfer, and associated methods and compositions, all of which comprise culturing a mammalian cell population containing cells at the G0/G1 stage of the cell cycle in media comprising at least a first antioxidant apoptosis inhibitor other than thioredoxin in an amount effective to increase the proportion of viable G0/G1 cells in the cell population; and fusing at least a first viable G0/G1 cell with an enucleated mammalian ovum.

In yet other embodiments, the use of uteroferrin is specifically excluded from the invention, so that the invention concerns methods of nuclear transfer, and associated methods and compositions, all of which comprise culturing a mammalian cell population containing cells at the G0/G1 stage of the cell cycle in media comprising at least a first apoptosis inhibitor other than uteroferrin in an amount effective to increase the proportion of viable G0/G1 cells in the cell population; and fusing at least a first viable G0/G1 cell with an enucleated mammalian ovum.

In still further embodiments, the use of α2-macroglobulin, thioredoxin and uteroferrin is specifically excluded from the invention, so that the invention concerns methods of nuclear transfer, comprising culturing a mammalian cell population containing cells at the G0/G1 stage of the cell cycle in media comprising at least a first apoptosis inhibitor other than α2-macroglobulin, thioredoxin or uteroferrin in an amount effective to increase the proportion of viable G0/G1 cells in the cell population; and fusing at least a first viable G0/G1 cell with an enucleated mammalian ovum.

The present invention also provides methods of cloning a mammal from a somatic or germ cell from a mammalian adult, fetus or embryo, comprising (a) culturing a population of mammalian somatic or germ cells containing cells at the G0/G1 stage of the cell cycle in media comprising an effective amount of at least a first apoptosis inhibitor for a period of time suitable to increase the proportion of viable G0/G1 cells in the population; and (b) generating a viable cloned mammal from at least a first of the viable G0/G1 cells.

This invention further provides methods of producing transgenic mammals, comprising (a) culturing a population of mammalian somatic or germ cells containing cells at the G0/G1 stage of the cell cycle in media comprising an effective amount of at least a first apoptosis inhibitor for a period of time suitable to increase the proportion of viable G0/G1 cells in the population; (b) introducing a selected DNA segment into viable G0/G1 cells of the cell population to produce viable transgenic G0/G1 cells; and (c) generating a transgenic animal from at least a first of the viable transgenic G0/G1 cells, wherein the selected DNA segment is contained and expressed in somatic and germ cells of the transgenic animal.

Whether "cloned" or "transgenic", various methods are available to "generate" the mammals from at least a first of the viable, optionally transgenic G0/G1 cells. For example, methods involving preparing blastocysts, preparing oocytes and preparing early stage embryos are included.

One may thus (a) fuse at least a first of the viable, optionally transgenic G0/G1 cells with an enucleated mammalian ovum (oocyte); (b) transferring the fused cell/ovum into a synchronized recipient mammalian female to produce a pregnant mammal; and (c) allowing gestation in the pregnant mammal to proceed for a period of time effective to allow the development of a viable cloned or transgenic mammal. Similarly, within step (a), one could (i) isolate a nucleus from the viable, optionally transgenic G0/G1 cells and (ii) inject the nucleus into an enucleated mammalian ovum (oocyte); and then continue with steps (b) and (c) as above.

Equally, the viable, optionally transgenic G0/G1 cells may be (a) injected into a blastocyst from a suitable mammal; followed by (b) transferring the blastocyst into a synchronized recipient female mammal to produce a pregnant mammal; and (c) allowing gestation in the pregnant mammal to proceed for a period of time sufficient to allow the development of a viable cloned or transgenic mammal.

Further, the viable, optionally transgenic G0/G1 cells may be (a) aggregated with an early stage embryo of a suitable mammal; followed by (b) transferring the embryo into a synchronized recipient female mammal to produce a pregnant mammal; and (c) allowing gestation in the pregnant mammal to proceed for a period of time sufficient to allow the development of a viable cloned or transgenic mammal.

The present invention further provides methods of producing a chimeric mammal from a somatic mammalian cell, comprising (a) culturing a population of somatic mammalian cells containing cells at the G0/G1 stage of the cell cycle in media comprising an effective amount of at least a first apoptosis inhibitor for a period of time suitable to increase the proportion of viable G0/G1 somatic cells in the population; (b) fusing at least a first of the viable G0/G1 somatic cells with an enucleated mammalian ovum; (c) culturing the fused cell/ovum in embryo media for a period of time effective to reach the morula/blastocyst stage of development; (d) combining the morula/blastocyst with a morula/blastocyst from a distinct mammalian species to form a morula/blastocyst aggregate; (e) transferring the morula/blastocyst aggregate into a synchronized recipient mammalian female to produce a pregnant mammal; and (f) allowing gestation in the pregnant mammal to proceed for a period of time effective to allow the development of a viable chimeric mammal.

Additionally, the present invention provides methods of producing mammalian cell lines. Using the present invention in conjunction with U.S. application Ser. No. 08/949,155, incorporated herein by reference, provides methods of preparing mammalian cell lines from somatic or germ cells, comprising (a) culturing a cell population comprising mammalian somatic or germ cells on an effective density of feeder cells and in a biologically effective culture medium comprising an amount of at least a first apoptosis inhibitor effective to increase the number of nuclear transfer competent cells in the cell population during culture; and (b) maintaining the cultured cell population for a period of time effective to provide a mammalian cell line.

The cell line methods of the present invention further include methods of producing a mammalian cell line from a somatic mammalian cell, comprising (a) culturing a population of mammalian somatic cells containing cells at the G0/G1 stage of the cell cycle in media comprising an effective amount of at least a first apoptosis inhibitor for a period of time suitable to increase the proportion of viable G0/G1 somatic cells in said population; (b) fusing at least a first of the viable G0/G1 somatic cells with an enucleated mammalian ovum; (c) culturing the fused cell/ovum in suitable media, such as embryo media, for a period of time effective to reach the morulalblastocyst stage of development, and (d) culturing the morula/blastocyst in suitable media, such as complete media, with or without a feeder layer and/or growth factors, for a period of time effective to allow the development of a mammalian cell line.

Yet further aspects of the invention include compositions, cell cultures and/or kits comprising cell culture media that comprise an amount of at least a first apoptosis inhibitor effective to increase the proportion of viable G0/G1 cells in a mammalian cell population and instructions for using the cell culture media to increase the proportion of viable G0/G1 cells in a mammalian cell population when cultured using the compositions, cell cultures and/or kits.

Other aspects of the invention are compositions, cell cultures and/or kits comprising a mammalian cell population containing cells at the G0/G1 stage of the cell cycle and a cell culture media that comprise an amount of at least a first apoptosis inhibitor effective to increase the proportion of viable G0/G1 cells in a mammalian cell population. Instructions for using the cell culture media to increase the proportion of viable G0/G1 cells in the mammalian cell population may be included in such compositions, cell cultures and/or kits.

The entire range of apoptosis inhibitors and combinations thereof, as exemplified herein in terms of the methods of the invention, may be used in the compositions and kits of the invention. In all such compositions, cell cultures and/or kits, further components may be included, such as DNA segments, vectors, feeder cells, various container and apparatus for confining the components. U.S. application Ser. No. 08/949,155 is specifically incorporated herein by reference for purposes of further describing such compositions, cell cultures and/or kits and their combination with other biological components and apparatus.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. Mammalian Cells

A. Adult Cells

Figure 1:
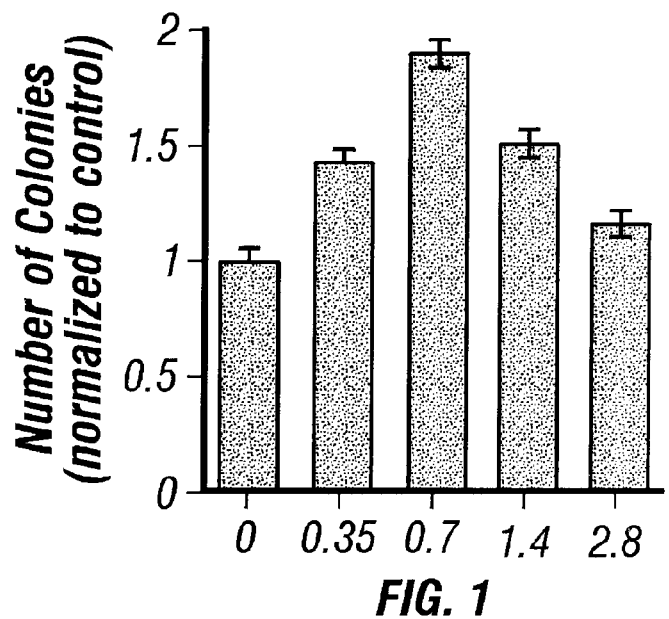
FIG. 1. Dose response to alpha-2-macroglobulin (MAC) of PGCs in culture. PGCs were cultured with various amounts (0, 0.35, 0.7, 1.4, or 2.8 pM; horizontal axis) of MAC, and the number of colonies (normalized to control; vertical axis) was determined.

Cells from any mammalian tissue can be used in the methods of the present invention, provided that they can be cultured as described herein. Exemplary of mammalian cells for use in the present invention are granulosa cells and mammary gland cells. Methods of obtaining such cells will be known to those of ordinary skill in the art in light of the present disclosure.

B. Embryonic Cells

Embryonic stem cells isolated from the inner cell mass of the preimplantation embryo possess the ability to proliferate indefinitely in an undifferentiated state, are capable of differentiating in vitro and in vivo, and can contribute to the formation of normal tissues and organs of a chimeric individual when injected into a host embryo. U.S. application Ser. No. 08/949,155 is specifically incorporated herein by reference for purposes of even further describing various embryonic stem cells suitable for use with the invention. Differentiation can be stimulated in vitro by modifying culture conditions, and in vivo by injection of ES cells into athymic mice (Doetschman et al, 1985). When allowed to differentiate in vitro, ES cells form structures known as embryoid bodies, which closely resemble the embryo-proper portion of the 5-day mouse embryo (Doetschman et al., 1985).

The ability to colonize the germ line following culture and genetic manipulation has made ES cells a powerful tool for the modification of the genome in the mouse species. Chimeras produced between genetically modified ES cells and normal embryos have been used to study in vivo gene regulation (Stewart et al., 1985) as well as germ-line transmission of introduced genes (Smithies, 1991). In addition, ES cells have been used to study targeted modification of genes by homologous recombination (Smithies, 1991; Piedrahita et al, 1992). Furthermore, mice have been cloned from ES cells (Wakayama et al., 1999).

Although the majority of the research on ES cells has been done in the mouse, attempts at developing the ES technology in other mammalian species have been reported by several investigators. Doetschman et al. (1988) showed that ES cells can be isolated from hamster embryos using feeders composed of murine primary embryonic fibroblasts. Several investigators using STO as feeder layers, have reported the isolation of porcine embryo-derived cell lines with ES-like morphology and a limited ability to differentiate in vitro and in vivo (Evans et al., 1990; Notarianni et al., 1990; Piedrahita et al., 1990; Strojek et al., 1990; Gerfen and Wheeler, 1995). In pigs, not only has it been demonstrated that injection of ICM into the blastocoele of a developing blastocyst results in chimeric pigs (Anderson et al., 1994; Onishi et al., 1994) but, additionally, there have been reports of the ability of cultured ICM-derived ES-like cells to contribute to the generation of a chimeric pig (Wheeler, 1994). However, not only the degree of reported chimerism was low, but to date there has been no report of germ line transmission of the ES genotype (Wheeler, 1994; Gerfen and Wheeler, 1995). Without germ line transmission, any genetic changes that have been introduced into the ES cell cannot be passed to the next generation and as a result, the animals have little, if any, practical value.

Recently, it has been reported that murine cell lines derived from primordial germ cells behave similarly to ES cells and are capable of contributing to the germ line (Labosky et al., 1994). These cells, referred to as EG cells or PGC-derived cells (Labosky et al., 1994; Strelchenko, 1996), are similar from ES cells in terms of markers of the undifferentiated state, as well as in their ability to colonize the germ line following injection into a host blastocyst (Labosky et al., 1994; Stewart et al., 1994). Thus, even though the starting tissue source or cellular phenotype differs from the ICM-derived cell lines, once established they have similar properties. Shim et al. (1997) have reported the ability of PGC-derived cell lines to contribute to the formation of a porcine chimera, demonstrating the pluripotential characteristics of these cell lines.

Results obtained with PGC (EG) derived cell lines indicate that they have a greater chance of being useful for transgenic modifications than embryo-derived ES cells. The reasons include: the ability to isolate 10,000 to 20,000 primordial germ cells from a single fetus (Shim and Anderson, 1995; published PCT patent application WO 98/16630, incorporated herein by reference), versus an average of 12–15 cells per embryo for ES cell isolation; the ability to obtain colonies with morphology and cellular markers typical of undifferentiated pluripotential cell lines at high frequency from the PGCs; the ability to maintain and passage the PGC colonies for a sufficient time that genetic modifications are permitted; the ability of PGC cell lines to contribute to the germ line of chimeras; and the potential use of EG cells as nuclear donors for embryo cloning studies.

Preliminary results with porcine inner cell mass indicates that injection of pluripotential EG cells into the blastocoele of the developing embryo have a good chance of transferring genetic changes through the germ line. The use of nuclear transfer with EG cell lines in ruminant species is based upon the technological advantages of using these embryos for nuclear transfer studies. To date is has not been possible to obtain any offspring from nuclear transfer studies in pigs beyond the 8-cell stage (Neimman and Reichelt, 1993). Nor, with few exceptions (Machaty et al., 1996), has it been possible to develop an in vitro oocyte maturation (IVM) system that can be used to generate oocytes suitable as nuclear recipients for nuclear transfers.

In contrast, studies in the bovine have indicated that nuclei from the inner cell mass of day 7 embryos are still capable of developing into a complete organism following nuclear transfer (Keefer et al., 1994). Additionally, the technology for IVM, IVF is well developed in bovine. Similarly, Campbell et al., (1996) recently reported that ability to generate live offspring from sheep embryo-derived cell lines after 13 passages in culture. As nuclear transfer studies have indicated that sheep and cattle are similar with respect to their timing of loss of totipotency (Smith and Wilmut, 1989; Keefer et al., 1994), it seems that cultured cattle embryo-derived cells will behave similarly to those from sheep.

1. Embryo Isolation

Embryos are collected from pregnant female animals of the selected mammalian species. The animals are either anesthetized, and the uterus is removed, or the embryos can be collected after slaughter. The embryos are usually collected very early in the gestational period. For example, porcine embryos are typically collected at day 25 of gestation, bovine embryos are typically collected at day 35–40 of gestation, and ovine and caprine embryos are typically collected on day 6 or 7 after estrus.

2. Isolation of Primordial Germ Cells

Once embryos have been collected, the primordial germ cells (PGCs) are isolated. Primordial germ cells are pluripotent cells that have the ability to differentiate into all three primary germ layers. In mammals, the PGCs migrate from the base of the allantois, through the hindgut epithelium and dorsal mesentery, to colonize the gonadal anlague (Eddy et al., 1981). The PGC-derived cells have a characteristically low cytoplasm/nucleus ratio, usually with prominent nucleoli. The PGCs are isolated from the embryos by removing the genital ridge of the embryo, dissociating the PGCs from the gonadal anlague, and collecting the PGCs. There are reports that the PGCs can be cryopreserved, with 60% viability 24 hours after thawing and culture (Leichthammer and Brem, 1990). Cryopreserved porcine PGCs are also capable of nuclear transfer (Liu et al., 1995).

Methods and compositions for use in isolating PGCs, culturing PGCs to produce primordial germ cell-derived cell lines, transforming such PGCs and cultured cell lines, and using the transformed cells and cell lines to generate transgenic animals with increased efficiency, thereby allowing the use of homologous recombination in producing transgenic non-rodent animal species, are described in co-pending U.S. application Ser. No. 08/949,155, filed Oct. 10, 1997. The entire disclosures of U.S. application Ser. No. 08/949,155, filed Oct. 10, 1997, U.S. Provisional Applications Ser. No. 60/027,338, filed Oct. 11, 1996, and Ser. No. 60/046,094, filed May 9, 1997, are incorporated herein by reference without disclaimer for the purposes of even further describing and enabling such techniques.

C. Fetal Cells

Among the preferred fetal cell types for use in the present invention are embryonic fibroblasts. Methods for isolation of embryonic fibroblasts are detailed below.

II. Culturing of Cells

In addition to the details herein, U.S. application Ser. No. 08/949,155 is specifically incorporated herein by reference for purposes of even further describing various methods and compositions, including media and feeder cells, suitable for culturing cells in conjunction with the present invention and for purposes of even further describing various methods of analyzing the cultured cells.

A. Serum Starvation Media

In addition to the media described elsewhere herein, serum starvation media for use in the present invention include any media suitable for culturing mammalian cells, with between 0.05% and 2% serum. Additional serum starvation media is described in Wilmut et al. (1997). A preferred media for serum starvation of cells includes DMEM with 2 mM glutamine, 0.1 mM β-mercaptoethanol, 1% penicillin/streptomycin solution and 0.5% FBS.

B. Embryo Media

Any number of standard basic or modified media have been described for culturing embryos from mammalian species, including, but not limited to, TCM199, BMOC, HF10 and NCSU based media. Such media are available commercially from sources such as GibcoBRL (Rockville, Md.).

C. Feeder Cells

Types of feeder cells that may be used in the present invention are embryonic cell lines such as murine $S1/S1^4$ or embryonic fibroblasts from selected animal species, such as porcine or bovine. More preferred for use in the present invention are STO cells (mouse embryonic fibroblast cells; Ware and Axelrad, 1972). In certain aspects of the invention, $S1^4$-m220 cells, which express only the membrane associated form of stem cell factor, may be used. The feeder cells provide growth factors to the growing primordial germ cells, but the amount of endogenous growth factors provided is variable from preparation to preparation. Therefore, exogenously added growth factors may be added to supplement the endogenous supply. Additionally, in particular aspects of the invention, the inventors contemplate engineering feeder cell lines to express selected growth factors, for example membrane-associated stem cell factor and basic fibroblast growth factor.

The feeder cells are inactivated prior to use, preferably by X-irradiation with agents such as cobalt or cesium, or using mitomycin C. The inactivated feeder cells are allowed to culture prior to use in culturing PCCs, preferably for 24 hours, but longer and shorter culture times are possible.

D. Media Composition

Preferred media for use in the present invention is low glucose Dulbecco's modified Eagle's media. Also preferred is Ham's F10 media. More preferred is a combination of low glucose Dulbecco's modified Eagle's media (about 50% v/v) and Ham's F10 media (about 50% v/v). Preferably, the media is supplemented with L-glutamine. Additional preferred media is supplemented with β-mercaptoethanol, and still other preferred media is supplemented with 100 nM of non-essential amino acids (L-alanine, L-asparagine, L-aspartic acid, L-glutamine, glycine, L-proline and L-serine; GIBCO). More preferred for use in the present invention is fully supplemented media, additionally comprising one or more of the following growth factors.

1. bFGF

A component of certain of the media compositions for use in the present invention is basic fibroblast growth factor (bFGF). bFGF is a member of the FGF family, currently composed of nine related mitogenic proteins that show 35–55% amino acid conservation. bFGF, unlike most of the other members of the family, lacks a signal peptide and is apparently secreted by mechanisms other than the classical protein secretory pathway. bFGF has been isolated from a number of sources, including neural tissue, pituitary, adrenal cortex, corpus luteum and placenta. bFGF contains four cysteine residues but reduced bFGF retains full biological activity. Several reports indicate that a variety of forms of bFGF are produced as a result of N-terminal extensions. These extensions apparently affect localization of bFGF in cellular compartments but do not affect biological activity. Recent studies indicate that binding of FGF to heparin or cell surface heparin sulfate proteoglycans is necessary for binding of FGF to high affinity FGF receptors.

bFGF stimulates the proliferation of all cells of mesodermal origin, and many cells of neuroectodermal, ectodermal and endodermal origin. The cells include fibroblasts, endothelial cells, astrocytes, oligodendrocytes, neuroblasts, keratinocytes, osteoblasts, smooth muscle cells and melanocytes. bFGF is chemotactic and mitogenic for endothelial cells in vitro. bFGF. induces neuron differentiation, survival and regeneration. bFGF has also been shown to be crucial in modulating embryonic development and differentiation. These observed in vitro functions of bFGF suggest that bFGF may play a role in vivo in the modulation of such normal processes as angiogenesis, wound healing and tissue repair, embryonic development and differentiation and neuronal function and neural degeneration. Additionally, bFGF may participate in the production of a variety of pathological conditions resulting from excessive cell proliferation and excessive angiogenesis.

The N-terminally truncated, 146 amino acid isoform of human bFGF has been cloned (Abraham et al., 1986). Recombinant human basic fibroblast growth factor expressed in *E. coli* is commercially available from R & D Systems (catalog#233-FB).

2. Uteroferrin

Uteroferrin is a purple colored, progesterone-induced glycoprotein containing two molecules of iron that is secreted by uterine endometrial epithelium of pigs (Bazer and Roberts, 1983; Roberts and Bazer, 1984). Uteroferrin exists as a 35,000 $M_r$ polypeptide having a purple color, and as a heterodimer ($M_r$=80,000) with one of three "uteroferrin-associated proteins" which have high amino acid sequence homology with serine protease inhibitors (Murray et al., 1989). The heterodimer has a rose color, but the biochemical and biological significance of the rose-form of uteroferrin and the uteroferrin-associated proteins is not known. Uteroferrin carries high mannose carbohydrate with the mannose-6-$PO_4$ recognition marker for lysosomal enzymes (Baumbach et al., 1984) and has acid phosphatase activity (Schlosnagle, et al., 1974). During pregnancy, uteroferrin is transported from uterine secretions into the fetal-placental circulation by specialized placental structures called areolae (Renegar et al., 1982). The mannose residues on uteroferrin are responsible for uteroferrin being targeted to reticuloendothelial cells of the fetal liver, the major site of hematopoiesis in fetal pigs (Saunders, et al., 1985).

Administration of radiolabeled iron to pigs results in endometrial secretion of uteroferrin carrying radiolabelled iron and incorporation of radiolabelled iron into fetal erythrocytes and cells of liver, spleen and bone marrow (Ducsay et al., 1982, 1984). Uteroferrin gives up its iron to fetal transferrin in allantoic fluid with a half-life of 12 to 24 hours (Buhi et al., 1982). Further, administration of iron dextran to pregnant pigs on days 50, 60 and 70 (term is at 115 days), the period of maximum secretion of uteroferrin by the endometrium, results in a 20% increase in iron stores in neonatal piglets (Ducsay et al., 1982, 1984). These results suggest a role for uteroferrin in transplacental transport of iron. However, after Day 75 of gestation, translation of mRNA for uteroferrin decreases rapidly (Simmen et al., 1988), secretion of uteroferrin by endometrial explant cultures declines (Basha et al., 1979), and the amount of uteroferrin in allantoic fluid decreases dramatically (Bazer et al., 1975). This suggests that an alternate mechanism for transplacental iron transport becomes operative between Days 75 and term when fetal/placental demands for iron are increasing (Ducsay et al., 1982, 1984).

Uteroferrin from pig uterus is a tartarate-resistant acid phosphatase with many properties in common with the Type 5 acid phosphatase in human placenta (Ketcham et al., 1985), chondrocytes of humans with osteoclastic bone tumors and spleens of humans with hairy cell leukemia, Gaucher's disease and Hodgkin's disease. In addition, uteroferrin has characteristics similar to those for purple acid phosphatases from bovine, rat, mouse, and pig spleen, as well as bovine milk, bovine uterine secretions, equine uterine secretions, and rat bone (Ketcham et al., 1985).

Uteroferrin and uteroferrin rose have been shown to aid in the stimulation of the proliferation of hematopoietic cells (Bazer and Gross, U.S. Pat. No. 5,258,367, incorporated herein in its entirety by reference). Uteroferrin and uteroferrin rose effect differentiation of primitive nonadherent hematopoietic stem cells in a non-species specific manner.

Uteroferrin and rose may be obtained by a variety of different methods. These substances may be obtained from uterine flushings of pigs (Baumbach et al., 1984; Murray et al., 1989) or allantoic fluid of pseudopregnant pigs (Baumbach et al., 1986). Human uteroferrin, also referred to as human placental Type V acid phosphatase, can be purified as described by Ketcham et al. (1985). Uteroferrin has also been produced by recombinant techniques (Simmen et al., 1988; Ketcham et al., 1989).

3. Membrane-associated SCF

It is believed, when used in certain aspects of the present invention, that inactivated feeder cells supply the cell culture with membrane-associated stem cell factor (SCF). Membrane-associated SCF lacks exon 6, which encodes a protease cleavage site. Feeder cells that provide membrane-associated SCF may be used in certain aspects of the present invention. Also preferred for use in certain aspects are feeder cells that have been engineered to overexpress membrane-associated SCF, or to solely express membrane-associated SCF.

4. Soluble SCF

Soluble stem cell factor (SCF) is another growth factor that may be used in particular embodiments of the present invention. SCF is a cytokine known to favor PGC survival and/or proliferation in vitro. SCF drastically reduces the incidence of apoptosis (programmed cell death) during the first hours of PGC culture (Pesce et al., 1993). C-kit ligand, the recently identified ligand for the kit tyrosine kinase receptor, is mapped to the mouse S1 locus. This pleiotropic cytokine, alternately known as stem cell factor (SCF), mast cell growth factor (MGF) and steel-factor (SLF), plays essential roles in gametogenesis, melanogenesis and early stages of hematopoiesis. In vitro and in vivo, SCF can stimulate the proliferation of mature, as well as the proliferation and maturation of immature, mast cells. On purified primitive human and mouse hematopoietic precursors, SCF acts in a synergistic manner with various growth factors, such as IL-1, IL-3, IL-6, IL-7, and Epo, to induce myeloid, erythroid and lymphoid lineage colony formation. The finding that SCF is also expressed in the nervous system suggests a possible role for SCF in the development of the nervous system.

The cDNA sequences for human, mouse and rat SCF encode transmembrane proteins that are composed of a signal peptide, a 189 amino acid extracellular domain, a hydrophobic transmembrane domain and an intracellular domain. Native SCF can exist either as the membrane bound form or as a soluble form of the first 164 or 165 amino acids of the extracellular domain. The soluble form is believed to be a proteolytic cleavage product of the transmembrane protein. Both the soluble and the transmembrane form of SCF have growth factor activities. Native soluble SCF is a heavily N- and O-glycosylated protein that exists as a non-covalently associated dimer in solution. All four cysteine residues of SCF monomers are involved in intramolecular disulfide bonds. Recombinant soluble SCF produced in E. coli is biologically active in in vitro bioassays, suggesting that glycosylation of the soluble form is not required for bioactivity in vitro. Murine or rat soluble SC is highly homologous to human soluble SCF (approximately 80%). Whereas both rat and mouse SCF are active on human cells, the human protein is much less active on mouse or rat cells.

The DNA sequence encoding the mature human SCF protein has been cloned (Martin et al., 1990). Recombinant human SCF from E. coli is available from R & D Systems (catalogue number 255-SC).

5. LIF

An additional growth factor that may be used in certain embodiments of the present invention is leukemia inhibitory factor (LIF). LIF is another cytokine that has also been shown to promote PGC survival by reducing apoptosis (Pesce et al., 1993). Leukemia inhibitory factor (LIF) was initially identified as a factor that inhibited the proliferation and induced the differentiation to macrophages of the murine myeloid leukemic cell line M1. Subsequent to its purification and molecular cloning, LIF was recognized to be a pleiotropic factor with multiple effects on both hematopoietic and non-hematopoietic cells. LIF has overlapping biological functions with OSM, IL-6, IL-11 and CNTF. All these cytokines utilize gp130 as a component in their signal transducing receptor complexes.

Human LIF cDNA encodes a 202 amino acid residue polypeptide with a 22 amino acid residue signal peptide that is cleaved to yield a 180 amino acid residue mature human LIF. Native human and mouse LIF are highly glycosylated monomeric proteins. Both human and murine LIF protein sequences have multiple potential N-and O-linked glycosylation sites and six conserved cysteine residues that are involved in three intramolecular disulfide bridges. The non-glycosylated, *E. coli*-expressed, recombinant human LIF is indistinguishable from native LIF in its biological activities in vitro. Human and murine mature LIF exhibit a 78% sequence identity at the amino acid level. Whereas human LIF is equally active on both human and mouse cells, murine LIF is approximately 1000 fold less active on human cells.

Recombinant human LIF, expressed in *E. coli* as a fusion protein with glutathione S-transferase (GST), cleaved from GST and HPLC purified, is commercially available from R & D Systems (catalogue number 250-L).

III. Transgene Compositions and Methods

In certain preferred embodiments of the invention, nucleic acids encoding transgenes of interest may be stably integrated into the genome of the cell or stably maintained in the cell as a separate, episomal segment of DNA. In addition to the details herein, U.S. application Ser. No. 08/949,155 is specifically incorporated herein by reference for purposes of even further describing various methods and compositions suitable for expressing gene constructs in cells in conjunction with the present invention.

For example, delivery of naked DNA or plasmids may be performed by any method that physically or chemically permeabilizes the cell membrane, such as via electroporation, calcium phosphate transformation or co-precipitation, DEAE-dextran treatment, particle bombardment, direct microinjection, sonication loading, liposome-mediated transformation, adenoviral assisted transfection, receptor-mediated transfection, or such like, as disclosed in U.S. application Ser. No. 08/949,155, specifically incorporated herein by reference. Other methods for delivery of transgenic constructs involve the use of vectors, such as adenovirus, adeno-associated virus (AAV), retrovirus, vaccinia virus, herpesviruses expression vectors, as also disclosed in U.S. application Ser. No.08/949,155, specifically incorporated herein by reference.

U.S. application Ser. No. 08/949,155 is also specifically incorporated herein by reference for purposes of even further describing the construction of vectors encoding transgenes for use in the present invention, including those encoding marker genes and/or therapeutic proteins, antisense constructs and/or ribozymes, and a range of suitable promoters, enhancers, reporter genes, homologous recombination and "knock-out" technology, detection methods and excision of transgenes.

In particular, U.S. application Ser. No. 08/949,155 is specifically incorporated herein by reference for purposes of even further describing exemplary classes of therapeutic genes for use in conjunction with the present invention, and biological functional equivalents thereof, such as those encoding inactivated tissue rejection components, proteins of immunological value, biopharmaceuticals and methods for the purification of recombinantly produced heterologous proteins. Animals that are resistant to certain diseases and pests; animals that have improved traits, such as modification of milk composition to increase shelf life, cheese yield and to permit lactose intolerant individuals to safely consume the modified milk, alteration of the growth rate, nutritional efficiency and carcass composition of animals, as well as items such as effecting wool composition; and animal models of human diseases can also be created, as disclosed in U.S. application Ser. No. 08/949,155, incorporated herein by reference.

U.S. application Ser. No. 08/949,155 is further incorporated herein by reference for purposes of describing changes in transgenes to improve expression by changing the sequence of the transgene to correspond to the codon usage of the particular host species selected. The information and tables concerning bovine, porcine and ovine codon preference are specifically incorporated herein by reference.

IV. Nuclear Transfer

Current methods of nuclear transfer in domestic species are derived from the method developed by McGrath and Solter (1983). The donor embryos and unfertilized recipient oocytes are treated with cytoskeletal inhibitors, a micropipette is inserted into the oocyte, and the metaphase chromosomes are removed in a portion of membrane-bounded cytoplasm. Successful enucleation is monitored by observing the removal of the chromosomes directly (Stice and Robl 1988), by indirect staining using the DNA-specific fluorescent dye bisbenzimide (Tsunoda et al. 1988; Prather and First 1990; Westhusin et al. 1990), or by mounting a portion of the enucleated oocytes and assuming an equal efficiency of enucleation in the remaining eggs (Willadsen 1986; Prather et al. 1987; Smith and Wilmut 1989). A single blastomere from the donor embryo (or portions thereof) is then aspirated into the micropipette and expelled into the perivitelline space, adjacent to the enucleated oocyte. The next step is the fusion of the two cells within the perivitelline space. This can be accomplished in some species with Sendai virus (Graham 1969) or with electrofusion (Berg 1982).

The efficiencies of the enucleation procedures can reach 100% when the chromosomes are directly or indirectly observed (Tsunoda et al. 1988; Stice and Robl 1988; Prather and First 1990), whereas the percentage of enucleated oocytes is lower when chromosomal removal is based solely on the location of the first polar body (Willadsen 1986; Prather et al. 1987; 1989).

Activation is thought to occur coincident with electrofusion. It has been known for many years that electrical pulses are an effective parthenogenetic agent in the mouse (Whittingham 1980). The specific mechanism of electrical activation is not known, but it may be related to membrane depolarization and calcium leakage after electrically induced pore formation (Whittingham 1980). As with fusion, electrically induced activation varies greatly from study to study. Factors that affect activation rates are many and include age and species of oocyte, type of chamber and medium in which the pulse is given, and type of pulse (Collas et al. 1989; Ozil 990).

Nuclear transfer involves obtaining single cells and fusing them to enucleated recipient ovum, effectively transferring the nucleus of the donor cell into the recipient cytoplasm. If successful, this reprograms the cell and instructs development of a new embryo that is genetically identical to that from which the cell was acquired. The significant potential of this technology was reported by Wilmut et al. (1997), indicating that nuclei from embryonic fibroblast and adult mammary epithelial cell can direct normal development in the sheep.

In addition to the scientific literature, PCT patent application WO 97/07669 (by Campbell and Wilmut), specifically incorporated herein by reference, concerns nuclear transfer methods. In describing the transfer of a quiescent donor cell into an enucleated recipient cell, WO 97/07669 favors the use of serum starvation to induce quiescence. However, other methods are explained to be useful in inducing quiescence, including chemical treatments, nutrient deprivation, growth inhibition or manipulation of gene expression (WO 97/07669). Any one or more of such methods may be used in preparing donor cells for use in the improved methods of the present invention. Indeed, the use of non-serum starved cells is further described in PCT patent application WO 99/01163, specifically incorporated herein by reference, the methods of which may also be used in combination with the invention described in the present application.

The nuclear transfer technique is less advanced in pigs, although there have been reports of successful births using nuclei from 4 cell embryos (Prather et al., 1989). PGCs collected from fetal tissue have also been successfully utilized as donors for nuclear transplantation (Cherny and Merei, 1994; Delhaise et al., 1995; Lavoir et al., 1997; Strelchenko, 1996). It has been demonstrated in pigs that previously cryopreserved PGCs can be used successfully as nuclear donors, giving rise to nuclear reprogramming and cleavage to the 4-cell stage (Liu et al., 1995). Ouhibi et al. (1996) reported nuclear reprogramming in cultured ICM-derived pig cells after nuclear transfer, although the ability of the embryos to participate in normal development was not studied.

In cows, Lavoir et al. (1997) reported 9–13% of cleaved nuclear transplant embryos developing to the blastocyst stage when oogonia collected from female fetuses (50–70 days gestation) were utilized as nuclei donors. Although no live calves were produced, an abnormal conceptus that developed in one animal was recovered by induced abortion and genetic analysis showed the fetus to be genetically identical to the donor oogonia. Similar results using bovine PGCs from both male and female fetuses have been reported by Moens et al. (1996). The observation by Strelchenko (1996) that nuclei from cultured bovine PGCs can direct development up to day 60 with no significant fetal abnormalities reported suggests that, when PGCs are placed in culture, nuclear changes occur that increase the nuclear potency of the cells when compared with freshly isolated PGCs.

An additional approach for increasing the contribution of the ES cell lines to the chimeric fetus has been the use of tetraploid embryos as hosts for the injection of ES cells. Using this approach, the developing tetraploid cells are restricted to the placental tissue while the diploid ES cells form the majority, if not all, of the fetus proper. While the original mouse cell lines used produced term offspring that died soon after birth (Nagy et al., 1990), use of other ES cell lines have resulted in chimeras with 100% ES contribution that survive to adulthood and breed normally (Ueda et al., 1995). In pigs, the ability of tetraploid embryos to form chimeric blastocysts when aggregated with diploid blastomeres has been demonstrated (Prather et al., 1996).

V. Blastocyst Injection

In this technique, blastocyst stage embryos are removed from pregnant females. The colonies derived from cultured cells are dissociated into single cells, and incubated with 2–5 blastocyst stage embryos. The mixture is then injected into the blastocoele of a developing embryo. After injection, the embryos are placed in an incubator and allowed to recuperate. The embryos are then returned to a recipient in an estrus stage 24 hours behind (later) than the donor embryo. An example is the use of day 6 donor embryos and day 5 recipients. Following transfer, the animals are monitored daily. Pregnancy is determined by non-return to estrus and ultrasound.

VI. Aggregation With Earlier Stage Embryos

Another way of making chimeras is to aggregate cells with earlier stage embryos, in particular 8 cell pre-compacted embryos. This is accomplished by either injecting 10–12 cells into the perivitteline space of an 8 cell stage embryo, and culture to the blastocyst stage to confirm incorporation of the cells into the ICM, or by removing the zona pellucida of the 8 cells embryo and placing the embryonic cells in close apposition with 8–12 cells. The .embryos are allowed to develop to the blastocyst stage to confirm incorporation of the cells into the ICM and transferred to recipient at the proper stage of the estrus cycle.

VII. Tetraploid Embryos

Another preferred approach for increasing the contribution of selected cells to a chimeric fetus has been the use of tetraploid embryos as hosts for the injection of the selected cells. Using this approach, the developing tetraploid cells are restricted to the placental tissue while the diploid selected cells form the majority, if not all, of the fetus proper. Tetraploid embryos are produced as described by Prather et al., (1996). Essentially, two cell embryos are collected at surgery from the oviduct after estrus detection and mating. Embryos are equilibrated and fused. After fusion, embryos are placed in Whitten's media and incubated for 6 days at 39° C. At this stage, the tetraploid embryos are used as host embryos. Following injection of 10–15 cells, embryos will be transferred to synchronized recipients and allowed to develop to term.

The following examples are included to demonstrate certain preferred embodiments of the invention. In addition to the examples that follow, the examples of U.S. application Ser. No. 08/949,155 are specifically incorporated herein by reference. It should be appreciated by those of skill in the art that the techniques disclosed in the examples that follow, and those of U.S. application Ser. No. 08/949,155, specifically incorporated herein by reference, represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

Improving the Efficiency of Nuclear Transfer In Mammalian Cells

A. Inventive Reasoning

Apoptosis is a natural phenomenon that can affect cells both in vivo and in vitro. The present Example provides compositions and techniques with demonstrated effectiveness in improving the culture and maintenance of PGCs in vitro, achieved by inhibiting apoptosis via the manipulation of the culture media. This Example therefore provides evidence of the successful execution of the invention in inhibiting apoptosis in G0/G1 cells prior to nuclear transfer. Thus, the methods and compositions described herein have applications in improving the culture and maintenance of primordial germ cells (PGC), improving the generation of transgenic and non-transgenic animals via PGC and chimeras, as well as in the generation of animals via nuclear transfer.

1. PGC Derived Cells

An observation on the effect of serpins (serine protease inhibitors) on the number of porcine PGC-derived colonies, encouraged the inventors to explore the potential role of this molecule in the inhibition of apoptosis in cultured PGCs. Early in vertebrate development, PGCs migrate from the hindgut to the genital ridge where, after active mitotic proliferation, they differentiate into gametes. However, when PGCs from 11.5–12.5 dpc mouse embryo are placed in culture in the absence of supporting feeder cells (Donovan et al., 1986), apoptosis is rapidly induced. The death of purified PGCs in vitro (Pesce et al., 1993; Pesce and De Felici, 1994) occurs with the morphological and biochemical hallmarks of apoptosis. Moreover, transformation of mouse PGCs with Bcl-Xl (Watanabe et al., 1997) resulted in a reduction of apoptosis and an increase in colony size, number of colonies, and the total number of cells.

To support the in vitro culture of mouse PGCs, supporting feeder cells expressing membrane bound stem cell factor (SCF) are required (Labosky et al., 1994, Strelchenko, 1996). Activation of the gp130 pathway by addition of LIF has been shown to increase expression of Bcl-xl (Fujio et al., 1997), as well as reduce the oxidative stress of the cell (Lotem et al., 1996). From their analysis of various studies, the inventors reasoned that the process of apoptosis is a normal phenomenon in cultured ES and PGCs, and that interfering with this process affects the ability to culture and maintain PGCs.

2. Nuclear Transplantation

The procedure of nuclear transfer involves obtaining single cells and fusing them to enucleated recipient ovum, transferring the nucleus of the donor cell into the recipient cytoplasm, to reprogram the cell and instruct the development of a new embryo that is genetically identical to that from which the cell was acquired. In the original study of Wilmut et al. (1997), and in many other publications since then, the donor cells have been placed in G0 prior to the nuclear transfer procedure. Serum starvation is often used to achieve the G0 stage.

The present inventors found that collection of cells from a serum starved population caused a large induction of apoptosis. This observation indicated to the inventors that a large proportion of nuclear donors that are being used for nuclear transfer are actually undergoing apoptosis and thus decreasing the overall efficiency of the process. Thus, the inventors reasoned that reduction of apoptosis in nuclear donor cells has a significant impact on the efficiency of the nuclear transfer procedure in all mammalian species by increasing the quality of the donor nuclei.

In studies analyzing the effects of added uteroferrin to cultured PGCs, the inventors observed a greater increase in efficiency of generating PGC-derived colonies when serpin bound uteroferrin was added compared to uteroferrin alone. A search of the existing literature indicated that serpins (serine protease inhibitors) have been implicated in the inhibition of apoptosis in a large number of cell types including PGCs (Dolci et al., 1993, Pesce and De Felici, 1994, Pesce et al., 1993, Tewari and Dixit, 1995).

However, despite the published reports that have now been interpreted in a consistent manner by the present inventors, the development of new biological techniques requires a demonstration of success in the intended study, not simply an interpretation of results with an inventive viewpoint. The inventors therefore tested the invention through the actual use of apoptosis inhibitors, rather than relying on an assessment of existing inefficient methods as perhaps including apoptosis as part of the mechanism(s) underlying their quantitative limitations. Accordingly, by actual positive data, rather than an informed interpretation of negative data, the present inventors herein show that the application of apoptosis inhibitors to PGCs in vitro is effective to significantly improve their culture and maintenance, thus providing an increased number of PGCs in G0/G1 that can be used successfully in nuclear transfer. The suitability of the invention in improving the generation of transgenic and non-transgenic animals via PGC and chimeras, as well as in the generation of animals via nuclear transfer, is thus demonstrated. Techniques for use in conjunction with the present invention are described in co-pending U.S. application Ser. No. 08/949,155, filed Oct. 10, 1997, specifically incorporated herein by reference.

A broad-range protease inhibitor, $\alpha$2-macroglobulin (Feige et al., 1996), was selected to verify that inhibition of the serine proteases in cultured PGCs leads to reduced apoptosis and increased efficacy of isolation of the colonies. The addition of $\alpha$2-macroglobulin to the culture media increased the number of first passage colonies as expected by the inventors. Additionally, there was a protective effect of $\alpha$2-macroglobulin upon second passage, independent of whether the cells had been cultured previously in the presence of this molecule. Therefore, addition of $\alpha$2-macroglobulin, or other protease inhibitors, to the media facilitates the ability to initially isolate colonies of cultured PGCs, and increases the efficiency with which long-term stable EG cell lines are established. Based on these results, other inhibitors of apoptosis were studied to determine the compound and the dose providing the greatest increase in efficiency. The inventors have identified apoptotic inhibitors that are effective in the isolation and long-term maintenance of cultured porcine PGCs. Among the preferred apoptosis inhibitors are protease inhibitors and anti-oxidants.

The inventors chose to study anti-oxidants based on the observation that increased oxidative stress leads to an increase in apoptosis in a large variety of cells (Hampton and Orrenius, 1997, Lotem et al., 1996), including mouse ES cells (Castro-Obregon and Covarrubias, 1996). Also, in light of the observation that expression of Bcl-2, an inhibitor of apoptosis, correlates with a decrease in oxidative stress (Tewari and Dixit, 1995) and that cytokine-dependent cells lines require a higher level of cytokine activation under conditions of oxidative stress (Lotem et al., 1996). Thus, the inventors reasoned that a high level of oxidative stress is a signal for induction of apoptosis under a variety of circumstances. Again, the present invention is supported by demonstrated successes in the intended study, not simply by assessment of data from an inventive perspective. Accordingly, anti-oxidants are herein shown to positively inhibit apoptosis such that the culture and maintenance of PGCs is improved, increasing the number of cells in G0/G1 for use in nuclear transfer and in the generation of transgenic and non-transgenic animals.

Initially, the antioxidants butylayed hydroxyanisole (BHA), cimetidine (CIM), N-t-butyl-$\alpha$-phenylnitrone (BPN), and N-acetylcysteine (NAC) were studied. These compounds are all commercially available, for example from Sigma (St. Louis, Mo.). As indicated above, NAC has a beneficial effect on mouse ES cells both under normal culture conditions as well as in the absence of BME. Moreover, the results indicated that the magnitude of increase in cell numbers in the presence of NAC is likely due to more than apoptosis inhibition as the % viable cells was not greatly affected. Other compounds of the same family were studied, based on the observation that some of the anti-oxidants described above had an even greater beneficial effect than NAC on apoptosis inhibition in a large variety of cells under different culture conditions (Lotem et al., 1996). The protocol for testing each compound is essentially as described herein for NAC.

In addition to studying the effects of anti-oxidants on apoptosis of ES cells, the role of protease inhibitors were also studied. The ICE-like proteases, recently named caspases, have been implicated in programmed cell death under a variety of different stimuli, including oxidative stress (Hampton and Orrenius, 1997), cytokine deprivation (Ohta et al., 1997), and normal embryonic development (Deveraux et al., 1997, Stack and Newport, 1997). In simple terms, ICE-like proteases are involved in later stages of apoptosis, downstream of the Bcl-2 and related family members. Inhibition of apoptosis by interfering with the family of proteases is herein shown by the inventors both in mouse ES cells and porcine PGCs.

To date at least 10 different ICE-like proteases or caspases have been identified and a large number of inhibitors have been described. Interestingly, serine protease inhibitors appear to be acting at a different level that the caspase-inhibitors, as has been recently demonstrated (Stefanis et al., 1997) by the observation that serpins were able to inhibit apoptosis by inhibiting activation of the caspases. As the inhibitors used are known not to inhibit members of the caspase family, the action of the serpins was upstream of caspase activation. This is important as the inventors reason that the earlier in the apoptotic cascade the event is blocked, the greater the likelihood that the cells will not suffer from any irreversible damage.

The inventors' initial studies concerned the compounds α-macroglobulin, AEBSF and TLCK. α-macroglobulin (MAC) is a broad spectrum protease inhibitor affecting cell survival and/or cell proliferation in mouse ES cells and porcine cultured PGCs and inhibits both serine and cysteine proteases. AEBSF (4-(2-aminoethyl) benzenesulfonyl hydrochloride) and TLCK (N-alpha-p-tosyl-L-lysine chloromethyl ketone), both inhibitors of serine proteases, block apoptosis triggered by trophic support (Stefanis et al., 1997).

B. Apoptosis Occurs During Isolation and Culture of PGCs

1. Collection of PGCs

Porcine fetuses were collected from hysterectomized uteri of four-way crossbred gilts (DeKalb, Ill.) between day 25 and 30 of pregnancy (estrus=day 0). Fetuses were washed in phosphate buffered saline supplemented with BSA (0.4%, Sigma St. Louis, Mo.) and penicillin/streptomycin (1%, Gibco BRL, Rockville, Md.) (PBS/BSA/PS). Urogenital ridges, appeared as longitudinal protrusions along the medial mesonephric surface, were isolated and washed in PBS/BSA/PS followed by several washes in PES medium before PGC collection. The PES medium was comprised of 50:50 mixture of Dulbecco's modified Eagle's medium (DMEM) and Ham's F10 medium supplemented with 15% fetal bovine serum (FBS), L-glutamine (2 mM), β-mercaptoethanol (0.1 mM), MEM non-essential amino acids (1%) and penicillin/streptomycin (1%). All media and supplements were purchased from Gibco BRL. FBS had been selected for its ability to maintain mouse ES cells, and was obtained from Summit Biotechnology (Fort Collins, Colo.).

PGCs were isolated by incubation in 0.25% trypsin/1 mM EDTA solution (Gibco BRL) followed by gentle pipetting or by mechanical dissociation of ridges into small fragments followed by gentle pipetting. After tissue disruption, cells were centrifuged for 5 minutes at 250 rpm to remove tissue debris and clumps. The supernatant containing most the single cells was collected and centrifuged at 1000 rpm for 10 minutes.

2. In vitro culture of PGCs and Maintenance of PGC-Derived Colonies

PGCs were resuspended with PES medium containing cytokines, such as soluble recombinant human stem cell factor (SCF; 40 ng/ml), human basic fibroblast growth factor (bFGF; 20 ng/ml), and human leukemia inhibitory factor (LIF; 20 ng/ml). All cytokines were obtained from R&D Systems (Minneapolis, Minn.). Cell suspensions were plated on irradiated mouse STO feeder cells ($3 \times 10^6$ cells per 35 mm well), prepared as previously described (Piedrahita et al., 1998) and cultured in humidified environment of 5% $CO_2$ in air, 38° C. PGC-derived colonies with ES-like morphology after 7–10 days of culture are passaged to fresh feeders for establishment of cell lines. PGC-derived colonies were dissociated with 0.25% trypsin/1 mM EDTA (Gibco BRL) for 10 minutes. Cells were observed at 24-hour intervals for changes in morphology using a Zeiss Axiovert 35 microscope. To identify PGC-derived cells and the state of differentiation were determined by morphology and by expression of alkaline phosphatase (AP).

3. AP Staining

AP activity was determined as described previously (Moore and Piedrahita, 1997). Briefly, culture plates were rinsed twice in PBS and fixed in 4% formaldehyde in PBS for 15 minutes at room temperature. Fixed cells were washed twice with PBS and stained in naphtol AS-MX phosphate (200 $\mu$g/ml; Sigma) and Fast Red TR salt (1 mg/ml; Sigma) in 100 mM Tris buffer, pH 8.2 for 30 minutes at room temperature. Staining was terminated by washing cultures in PBS. Specificity of AP activity was determined by staining in the presence of the AP inhibitor, tetramisole (500 $\mu$M; Sigma). Mouse ES cells also were stained as control for AP activity.

4. Stage-Specific Embryonic Antigen-1 (SSEA-1) Staining

Porcine PGCs and PGC-derived colonies were stained for expression of SSEA-1. Monoclonal antibody to SSEA-1 (Developmental Studies Hybridoma Bank, University of Iowa) was diluted 1:10 in PBS supplemented with 5% goat serum (Gibco BRL). Goat serum diluted 1:10 with PBS was applied to slides or tissue culture wells for 30 minutes at room temperature for blocking of nonspecific background staining, followed by the primary antibody and incubation for 1 hour at room temperature or 4° C. overnight. To identify primary antibody, Vectastain ABC kit (Vector Laboratories, Burlingame, Calif.) was used according to manufacturer's instruction. Briefly, cells were incubated with biotinylated-secondary antibody solution for 30 minutes and washed with PBS. Then, avidin conjugated with alkaline phosphates was applied and color reaction was performed with substrate solution. Specificity of SSEA-1 expression was determined by staining in the absence of the primary antibody.

5. TUNEL Assay

Freshly isolated or cultured PGCs were attached to poly-L-lysine coated slides and fixed in 1% paraformaldehyde in PBS, pH 7.2 for 10 minutes at room temperature. After 2 washes with PBS, cells were stained according to protocols with the ApopTag kit (Intergen, Purchase, N.Y.). Briefly, cells were treated with equilibration buffer and stained in labeling solution containing dioxigenin-dNTP and TdT (terminal deoxynucleotidyl transferase) for 60 minutes at 37° C. TdT catalyzes a template-independent addition of dioxigenin-dNTP to the 3'-OH end of DNA breaks. After termination of reaction and several washes, cells were incubated with an anti-dioxigenin antibody conjugated to peroxidase for 30 minutes at room temperature. After wash with PBS, peroxidase substrate, 3, 3'-diaminobenzidine (DAB) applied and waited for 5 minutes for color development (brown color localized at nucleus). After counterstaining with 0.5% methyl green for 10 minutes at room temperature, slides were dehydrated using n-butanol and mounted for analysis under the light microscopy.

The in situ TUNEL assay was used to detect apoptosis of cultured porcine PGCs when freshly isolated and after 6 hours of culture. A color change to brown/red cells is indicative of cells undergoing apoptosis. In comparing freshly isolated PGCs against PGCs after 6 hours culture, there is an increase in the number of brown/red cells. This study directly shows that PGCs in culture undergo apoptosis.

6. Light and Transmission Electron Microscopy

Porcine PGCs were cultured in suspension with PES medium at 2 hours interval up to 6 hours. Cells were collected, washed with PBS, pelleted, and fixed at 4° C. overnight in 1 ml Karnovsky's glutaraldehyde-formaldehyde in 0.1 M sodium cacodylate buffer. After fixation, pellets were washed three times for 15 minutes each in 0.1 M sodium cacodylate buffer and postfixed in 1% $OsO_4$ in 0.1 M sodium cacodylate buffer for 2 hours at room temperature. After rinsing 3 times each with 0.1 M sodium cacodylate buffer and water, pellets were incubated with uranyl acetate overnight at 4° C. and performed dehydration in a graded series of ethanol from 50–100% followed by washing in propylene oxide, three times for 15 minutes. Infiltration was with a 1:1 mixture of propylene oxide:Epon Araldite overnight and 100% Epon Araldite for 4 hours. Embedding in 100% Epon Araldite was done at 56° C. for 48 hours. Sections were cut, dried, and stained with toluene blue for visualization under the light microscope, while ultra-thin sections were stained with uranyl acetate for 12 minutes, lead citrate for 12 minutes, and viewed with a transmission electron microscope after drying.

Electron microscopy of cultured porcine PGCs showed the progression of apoptosis during culture. Freshly isolated PGCs were plated on plastic and analyzed every 2 hrs. Freshly isolated PGC showed typical morphology with large nucleus to cytoplasm ratio. After 2 hr of culture, chromatin started to condense. After 4 hr, nuclear fragmentation is seen. By 6 hr, the cells are undergoing the last stages of apoptosis with complete cellular fragmentation and the formation of apoptotic bodies. This demonstrates that porcine PGCs in culture undergo apoptosis and reinforces the foregoing results obtained using the TUNEL assay.

C. Effect of Apoptosis Inhibitors on Isolation and Culture of PGCs

1. In vitro Culture of Porcine PGCs with Apoptosis Inhibitors

To determine the effect of apoptosis inhibitors on survival of porcine PGCs in vitro, freshly isolated PGCs were cultured as described above with or without apoptosis inhibitors, $\alpha_2$-macroglobulin (MAC: broad range protease inhibitor, 1.4 pM) and N-acetylcysteine (NAC: antioxidant, 1 mM). After 7–10 days of culture, colonies were stained for AP activity and counted. Studies were performed at least three replicates. The data were normalized to the treatment with no inhibitors added (control) and tested for homogeneity of variance and analyzed by ANOVA. Mean separation is accomplished by Fisher's protected LSD using software SuperANOVA (Abacus Concepts).

Dose titration of MAC (0.35, 0.7, 1.4, and 2.8 pM) and NAC (0.25, 0.5, 1.0, and 2.0 mM), to determine the optimal concentration of inhibitors, were performed. Also, other protease inhibitors such as pepstatin A (PA, 50 µM), 4-(2-aminoethyl)benzenesulfonyl fluoride (AEBSF, 250 µM), and Nα-p-tosyl-L-lysine chloromethyl ketone (TLCK, 100 µM), and other antioxidants such as butylated hydroxyanisole (BHA, 0.1 mM), N-t-butyl-α-phenylnitrone (BPN, 1.0 mM), cimetidine (CIM, 2.0 mM), and glutathione (GSH, 2.0 mM), were tested to determine the effects on survival of porcine PGCs in vitro.

After culture, colonies were stained, counted and analyzed as described above. To determine the effects of MAC and NAC on porcine PGCs, cells were exposed to those inhibitors during the first half period of culture (4–5 days) or the last half period (4–5 days), respectively. In addition, to determine the effect of MAC and NAC in the absence of feeders, cells were plated on chambered slides previously coated with 0.1% gelatin and medium with or without inhibitors in the presence or absence of growth factors. Cells were fixed, stained for AP and counted at the interval of 24, 48, and 72 hours.

2. Dose Response to Alpha-2-macroglobulin, Protease inhibitor

The following study was conducted:

TABLE 1

| Treatment | Normalized # of Colonies + SE | P Value compared to control |
| --- | --- | --- |
| No MAC (Control) | 1 | |
| 0.35 pM MAC | 1.43 ± 0.03 | 0.0001 |
| 0.7 pM MAC | 1.90 ± 0.08 | 0.0001 |
| 1.40 pM MAC | 1.50 ± 0.01 | 0.0001 |
| 2.8 pM MAC | 1.16 ± 0.06 | 0.0388 |

The results of the study are shown in FIG. 1. Maximal response to MAC is seen at 0.7 pM concentration. Higher concentrations are effective, but less than maximum.

3. Dose Response to N-Acetyl Cysteine, Anti-Oxidant

The following study was conducted:

TABLE 2

| Treatment | Normalized # of Colonies + SE | P Value compared to control |
| --- | --- | --- |
| No NAC (Control) | 1.0 | |
| 0.25 mM NAC | 1.23 ± 0.14 | 0.2382 |
| 0.5 mM NAC | 1.75 ± 0.13 | 0.0026 |
| 1.0 mM NAC | 2.07 ± 0.19 | 0.0002 |
| 2.0 mM NAC | 2.21 ± 0.04 | 0.0002 |

Figure 2:
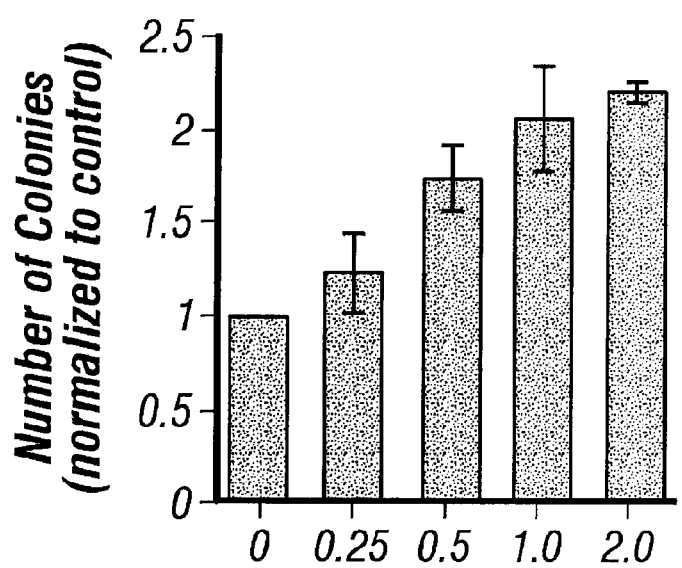
FIG. 2. Dose response to N-acetyl cysteine (NAC) of PGCs in culture. PGCs were cultured with various amounts (0, 0.25, 0.5, 1.0, or 2.0 mM; horizontal axis) of NAC, and the number of colonies (normalized to control; vertical axis) was determined.

The results of the study are shown in FIG. 2. The maximal response over the doses studied is seen at 2.0 mM, but it is reasoned that likely that concentrations higher than 2.0 mM will be equally, if not more, effective.

4. Combined Effects of MAC and NAC

The following study was conducted:

TABLE 3

| Treatment | Normalized # of Colonies + SE | P Value compared to control |
|---|---|---|
| No MAC or NAC (Control) | 1.0 | |
| MAC alone 0.7 pM | 2.00 ± 0.18 | 0.0026 |
| NAC alone 1.0 mM | 2.73 ± 0.03 | 0.0003 |
| MAC + NAC (0.7 pM and 1 mM) | 3.17 ± 0.1 | 0.0001 |

Figure 3:
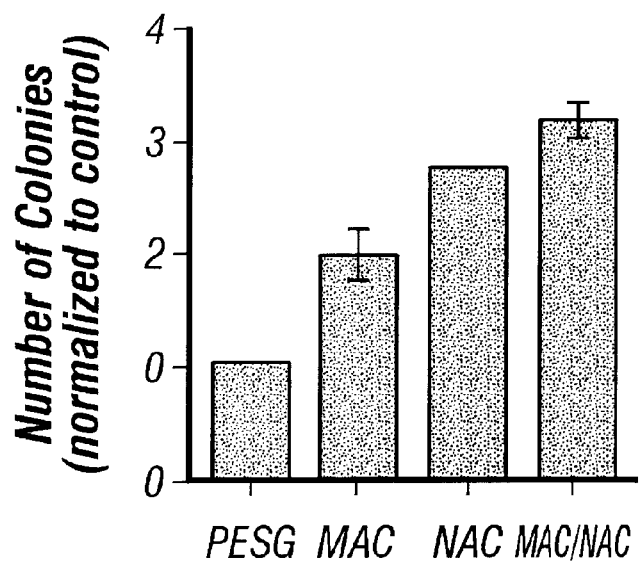
FIG. 3. Combined effect of alpha-2-macroglobulin (MAC) and N-acetyl cysteine (NAC) of PGCs in culture. PGCs were cultured with no MAC or NAC (PESG), MAC alone (0.7 pM), NAC alone (1.0 mM) or MAC (0.7 pM) plus NAC (1.0 mM), and the number of colonies (normalized to control; vertical axis) was determined.

The results are shown in FIG. 3. There is an additive effect when using both MAC and NAC over each agent alone.

5. MAC Timing of Exposure Response (First 4 Days vs. Last 4 Days)

The following study was conducted:

TABLE 4

| Treatment | Normalized # of Colonies + SE | P Value compared to control |
|---|---|---|
| No MAC (Control) | 1.0 | |
| MAC all 8 days | 1.64 ± 0.08 | 0.0001 |
| MAC 1–4 days (FH) | 1.21 ± 0.05 | 0.0467 |
| MAC 5–8 days (LH) | 1.23 ± 0.09 | 0.0302 |

Figure 4:
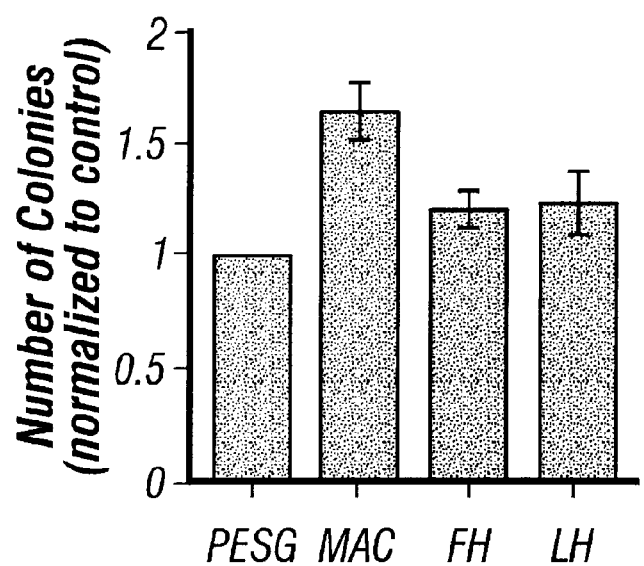
FIG. 4. Timing of alpha-2-macroglobulin (MAC) of PGCs in culture. PGCs were cultured without MAC (PESG), or with MAC (0.7 pM) for all 8 days (MAC), the first 4 days (FH), or the last 4 days (LH), and the number of colonies (normalized to control; vertical axis) was determined.

The results are shown in FIG. 4. Although effective at early and late stages, maximal effects result when MAC is present throughout the incubation period.

6. NAC Timing of Exposure Response (First 4 Days vs. Last 4 Days)

The following study was conducted:

TABLE 5

| Treatment | Normalized # of Colonies + SE | P Value compared to control |
|---|---|---|
| No NAC (Control) | 1.0 | |
| NAC all 8 days | 2.64 ± 0.49 | 0.0080 |
| NAC 1–4 days (FH) | 2.86 ± 0.55 | 0.0037 |
| NAC 5–8 days (LH) | 1.01 ± 0.035 | 0.9811 |

Figure 5:
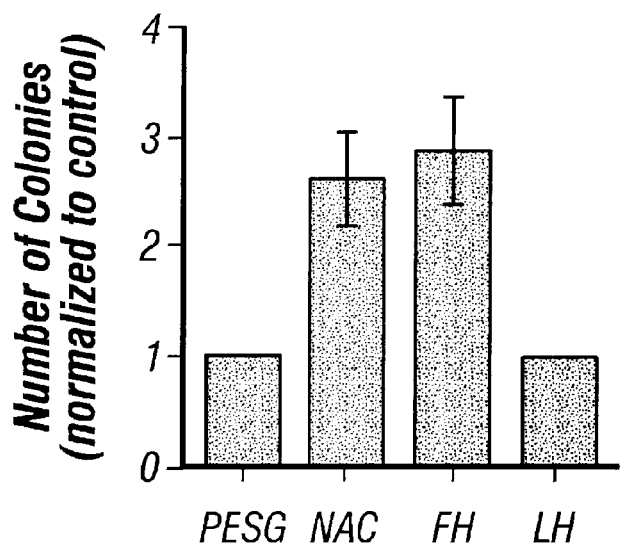
FIG. 5. Timing of N-acetyl cysteine (NAC) of PGCs in culture. PGCs were cultured without NAC (PESG), or with NAC (1.0 mM) for all 8 days (NAC), the first 4 days (FH), or the last 4 days (LH), and the number of colonies (normalized to control; vertical axis) was determined.

The results are shown in FIG. 5. NAC should be present during the initial stages of incubation to have its effect. Addition at later days has little effect on the cultured PGCs.

7. Study Using Different Protease Inhibitors

The following study was conducted:

TABLE 6

| Treatment | Normalized # of Colonies + SE | P Value compared to control |
|---|---|---|
| No inhibitors (Control) | 1.0 | |
| MAC 0.7 pM | 1.72 ± 0.15 | 0.0002 |
| PA 50 μM | 0.85 ± 0.13 | 0.2053 |
| AEBSF 250 μM | 1.14 ± 0.07 | 0.3568 |
| TLCK 100 μM | 1.21 ± 0.10 | 0.1743 |

Figure 6:
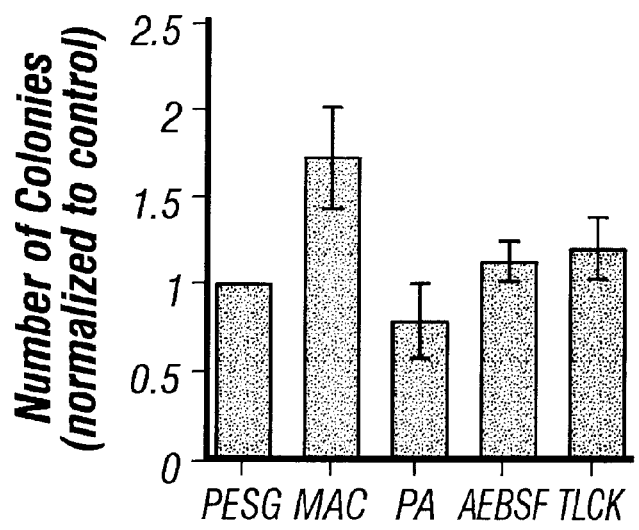
FIG. 6. Effect of different protease inhibitors on PGCs in culture. PGCs were cultured without protease inhibitors (PESG), with alpha-2-macroglobulin (MAC; 0.7 pM), pepstatin A (PA, 50 $\mu$M), 4-(2-aminoethyl)benzenesulfonyl fluoride (AEBSF, 250 $\mu$M), and N$\alpha$-p-tosyl-L-lysine chloromethyl ketone (TLCK, 100 $\mu$M), and the number of colonies (normalized to control; vertical axis) was determined.

The results are shown in FIG. 6. Of the protease inhibitors tested, MAC induced the most, and significantly, positive effect on the number of PGCs. AEBSF and TLCK also had a positive effect. The inventors reason that results using AEBSF and TLCK are likely to be improved by performing a dose response study.

8. Study Using Different Antioxidants

The following study was conducted:

TABLE 7

| Treatment | Normalized # of Colonies + SE | P Value compared to control |
|---|---|---|
| No inhibitors (Control) | 1.0 | |
| NAC 1.0 mM | 1.93 ± 0.10 | 0.0006 |
| BHA 0.1 mM | 2.48 ± 0.27 | 0.0001 |
| BPN 1.0 mM | 1.95 ± 0.17 | 0.0004 |
| CIM 2.0 mM | 1.95 ± 0.05 | 0.0004 |

Figure 7:
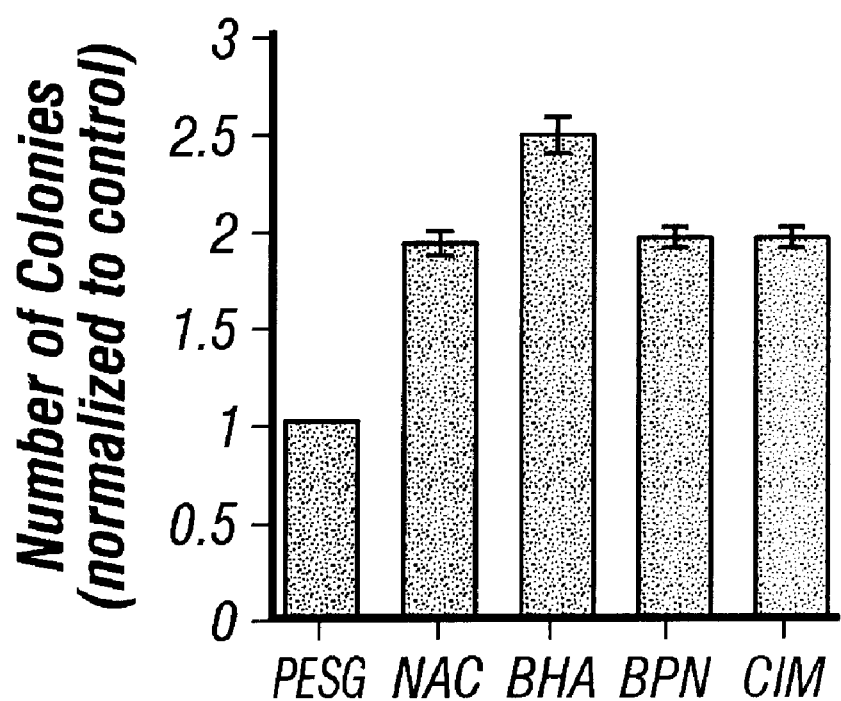
FIG. 7. Effect of different antioxidants on PGCs in culture. PGCs were cultured without antioxidants (PESG), with N-acetyl cysteine (NAC; 1.0 mM), butylated hydroxyanisole (BHA, 0.1 mM), N-t-butyl-$\alpha$-phenylnitrone (BPN, 1.0 mM), or cimetidine (CIM, 2.0 mM), and the number of colonies (normalized to control; vertical axis) was determined.

The results are shown in FIG. 7. All anti-oxidants tested had significant positive results on the number of PGCs. Even without a dose response analysis, the beneficial effect is clear and could likely be further improved by doing a dose response for each compound.

9. MAC and NAC Effects on PGCs in the Absence of Feeder Layers

Freshly isolated PGCs were plated in chambered slides in the absence of feeders and incubated in media with or without growth factors (GF) and with or without MAC and NAC. Cells were fixed, stained for AP as previously described, and counted.

Figure 8:
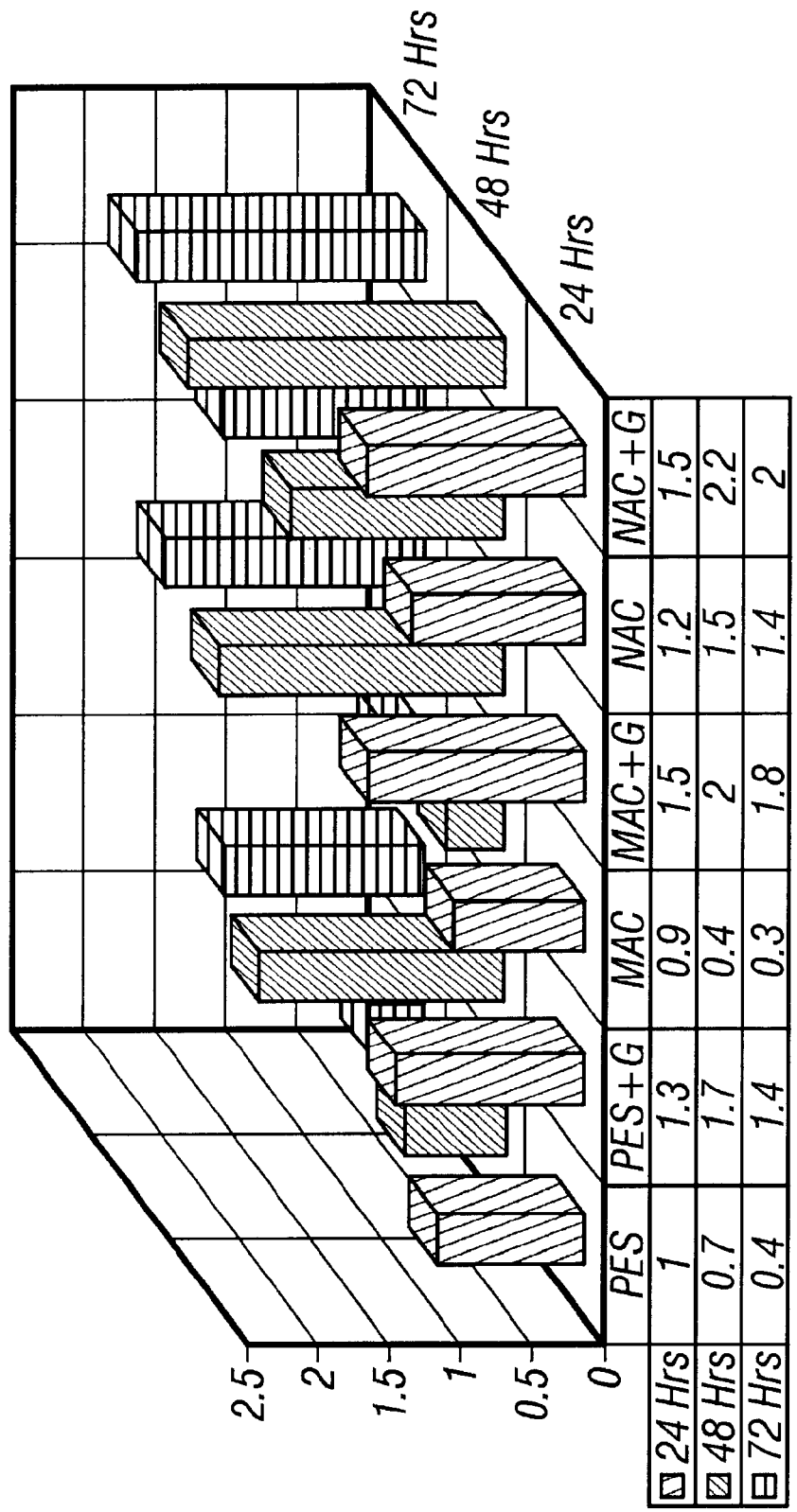
FIG. 8. Freshly isolated PGCs were plated in chambered slides in the absence of feeder cells and incubated in media with no protease inhibitors or antioxidants (PES), with MAC (MAC) or with NAC (NAC), either with or without growth factors (G), for 24, 48 or 72 hours. Cells were fixed, stained for alkaline phosphatase (AP) as previously described, and counted (normalized to control; left vertical axis).

The results are shown in FIG. 8. Addition of MAC and NAC increased the number of PGCs surviving in culture in the absence of feeder layers. Addition of growth factors had a stimulatory effect of survival of PGCs. NAC was able to rescue the PGCs even in the absence of growth factors even after 72 hr of culture.

In each of the foregoing studies, the morphology and AP staining pattern of the cells in the presence of apoptosis inhibitors were not different to those in the controls. These studies show that apoptosis inhibitors increase the number of viable cells available for further manipulation, including in homologous recombination and gene targeting, which require large numbers of cells.

D. Results of the Effect of Apoptosis Inhibitors on Serum Starved Fibroblasts

Porcine embryonic fibroblast (PEF) were isolated from day 25–28 fetuses according to the methods previously described (Hogan et al., 1994). Briefly, porcine fetuses of day 25–30 (day 0=estrus) were removed from the uterus and rinsed with PBS+penicillin/streptomycin solution (PBS/PS). Head, limbs and internal organs were removed, and the carcasses were minced with razor blades or ground using a syringe head until they were the consistency of sludge. Then these were trypsinized 2–3 times using 0.25% trypsin+ EDTA for 20 minutes. The supernatant fraction was removed and centrifuged to collect the cells. The cells were plated using DMEM+10% fetal bovine serum (FBS) and cultured up to 80–90% confluency before further passage.

Bovine embryonic fibroblasts (BEF) were isolated from the fetus with 3–5 cm crown-rump length. After two or three passages, cells were plated one million cells per plate (100 mm) with growth medium (DMEM) with 2 mM L-glutamine, 0.1 mM β-mercaptoethanol and 10% FBS. After 24 hours, cells were washed with PBS 3–5 times and then serum starvation medium with 0.5% FBS was added. In addition, cells were treated with serum starvation medium containing apoptosis inhibitors such as $a_2$-macroglobulin (0.7 pM), N-acetylcysteine (1 mM) and glutathione (2 mM). Cells were treated with serum starvation with or without apoptosis inhibitors for 5 or 10 days. Then cells were trypsinized and counted.

1. TUNEL Assay

After counting, cells were fixed and stained according to protocols with the APO-BRDU kit (Phoenix Flow Systems, San Diego, Calif.). Briefly, cells were fixed in 1% paraformaldehyde in PBS on ice for 15 minutes, washed in PBS, and fixed in 70% ethanol and stored at −20° C. until use. After removing the fixative, cells were washed twice and suspended in 50 μl of labeling solution containing Br-dUTP (bromolated deoxyuridine triphosphate) and TdT (terminal deoxynucleotidyl transferase) for 60 minutes at 37° C. TdT catalyzes the addition of Br-dUTP to the 3'-OH ends of DNA strand breaks in a template independent manner. To determine base line fluorescence, control cells were incubated without TdT. After rinsing, cells were incubated with an anti-BrdU monoclonal antibody conjugated to fluorescein for 30 minutes in the dark at room temperature; apoptotic cells which contain many free 3'-OH ends are intensely labeled, while non-apoptotic cells whose DNA is largely intact have little Br-dUTP incorporation and remain unlabeled. Following counterstaining with a propidium iodide/RNase A solution for 30 minutes in the dark, which allows simultaneous analysis of cell cycle position and apoptosis, cells were analyzed on a FACSCalibur™ flow cytometer (Becton Dickinson, San Jose, Calif.). Fluorescence emissions were measured at 582±21 nm for propidium iodide and 530±15 nm for fluorescein, without spectral compensation, after excitation at 488 nm by an argon-ion laser. For analysis, gates were set so that less than 2% of samples incubated without TdT were positive. Any event above this gate was deemed TUNEL positive for samples incubated with TdT.

2. Propidium Iodide

Cells ($1 \times 10^6$) were washed in 0.15 M NaCl, fixed in 70% ethanol, and stored at −20° C. overnight or until ready to be analyzed. For analysis, cells were centrifuged, rinsed with PBS, resuspended in 500 μl of a 0.05 mg/ml propidium iodide/0.1% Triton X-100/0.2 mg/ml RNase A solution, and incubated for a minimum of 30 minutes at room temperature in the dark. Cells were analyzed by flow cytometry to determine DNA content. Modfit LT™ (Verity Software House, Topsham, Me.) was used to model the cell cycle distribution within each sample.

3. Response of Bovine Embryonic Fibroblasts (BEF) to Apoptosis Inhibitors

To show the induction of G0 in BEF by serum starvation and the effects of different apoptosis inhibitors, the following study was conducted:

TABLE 8

| Treatment | G0/G1 (%) | S (%) | G2/M (%) |
|---|---|---|---|
| BEF control* | 47 | 38 | 15 |
| BEF serum starved | 90 | 8 | 2 |
| SS + MAC | 85 | 5 | 10 |
| SS + NAC | 88 | 2 | 10 |
| SS + GSH | 86 | 4 | 10 |

Serum starvation for 5 days increases the number of cells in G0/G1 to 90%, indicating treatment is indeed placing cells in a G0 state. Addition of MAC, NAC, or GSH during the starvation period did not affect the proportion of cells going into G0.

To show the effect of apoptosis inhibitors on the rate of apoptosis in BEF following serum starvation (G0 Induction) for 5 or 10 days, the following study was conducted:

TABLE 9

| Treatment | 5-day Apoptosis (%) | 10-day Apoptosis (%) |
|---|---|---|
| BEF Control* | 2.8 | 2.8 |
| BEF serum starved | 15.0 | 20.4 |
| SS + MAC | 3.9 | 4.6 |
| SS + NAC | 1.8 | 1.1 |
| SS + GSH | 1.5 | 0.8 |

Addition of apoptosis inhibitors during serum starvation reduces the proportion of cells undergoing apoptosis. Both protease inhibitors and anti-oxidants have a beneficial effect, although the anti-oxidants show a greater response.

4. Response of Porcine Embryonic Fibroblasts (PEF) to Apoptosis Inhibitors

To show the induction of G0 in PEF by serum starvation and effects of different apoptosis inhibitors, the following study was conducted:

TABLE 10

| Treatment | G0/G1 (%) | S (%) | G2/M (%) |
|---|---|---|---|
| PEF control* | 51 | 35 | 14 |
| PEF serum starved | 95 | 1 | 4 |
| SS + MAC | 95 | 1 | 4 |
| SS + NAC | 95 | 2 | 3 |
| SS + GSH | 95 | 2 | 3 |

Serum starvation for 5 days increases the number of cells in G0/G1 to 95%, indicating treatment is indeed placing cells in a G0 state. Addition of MAC, NAC, or GSH during the starvation period did not affect the proportion of cells going into G0.

To show the effect of apoptosis inhibitors on the rate of apoptosis of porcine fibroblasts following serum starvation (G0 Induction) for 5 Days, the following study was conducted:

TABLE 11

| Treatment | 5-day Apoptosis (%) |
|---|---|
| PEF control* | 0.17 |
| PEF serum starved | 26.50 |
| SS + MAC | 11.60 |
| SS + NAC | 0.06 |
| SS + GSM | 0.12 |

Addition of apoptosis inhibitors during serum starvation reduces the proportion of cells undergoing apoptosis. Both protease inhibitors and anti-oxidants have a beneficial effect, although the anti-oxidants show a greater response.

EXAMPLE II

Apoptosis Inhibitors

Given the foregoing successful studies, various apoptosis inhibitors, protease inhibitors and anti-oxidants can now be used to increase the efficiency of nuclear transfer, produce cell lines, chimeric cell lines, and transgenic and non-transgenic mammals from such cells and cell lines. A number of proteins have been shown to inhibit apoptosis, or programmed cell death (Pesce et al., 1993), any one or more of which can now be used in such methods. Growth factors that inhibit apoptosis promote primordial germ cell survival, so this class of proteins is particularly preferred for use in the present invention. α2-macroglobulin is a particularly preferred example of an apoptosis inhibitor for use in certain aspects of the present invention. Also representative of this class are oncogenic proteins such as bcl-2 and family members including Bcl-x1, Mcl-1, Bak, A1, A20, and inhibitors of interleukin-1β-converting enzyme and family members. Preferred for use is bcl-2 (distinct from bcl-1, cyclin D1; GenBank Accession No. M14745, X06487). Overexpression of this oncogene was first discovered in T-cell lymphomas. It functions as an oncogene by binding and inactivating bax, a protein in the apoptotic pathway.

A number of additional factors are contemplated for use in the present invention, based on their ability to block, prevent, or reduce apoptosis. The calcium ionophore A23187 has been shown to block apoptosis in certain systems, such as when interleukin-3 (IL-3) is withdrawn from IL-3 dependent cells. N-Acetyl-L-cysteine has been shown to prevent apoptotic death of neuronal cells (Ferrari et al., 1995) and TNF-α induced apoptosis in U937 cells (Cossarizza et al., 1995). Nakajima et al. (1994) showed that actinomycin D, while a potent inducer of apoptosis in many cell lines, has been shown to suppress programmed cell death of PC12 cells induced by etoposide, an inhibitor of topoisomerase II. These studies also showed that cycloheximide, nerve growth factor and epidermal growth factor also rescued PC12 cells from etoposide-induced death. Insulin-like growth factor-I (IGF-1) and the IGF-1 receptor were also shown to inhibit etoposide-induced apoptosis in BALB/c 3T3 cells (Sell et al., 1995).

3-Aminobenzamide has been shown to be an inhibitor of UV-induced apoptosis (Malorni et al., 1995). Aphidocolin potentiates apoptosis induced by arabinosyl nucleosides in leukemia cell lines, and inhibits vincristine-induced apoptosis in the p53-negative human prostate cancer cell line PC-3 (Borner et al., 1995). L-Ascorbic acid (vitamin C), catalase, follicle stimulating hormone, N-acetyl-L-cysteine, vasoactive intestinal peptide, cyclic GMP, hCG, interleukin-1β (IL-1β) and superoxide dismutase have all been shown to inhibit or suppress apoptosis in cultured rat ovarian follicles (Flaws et al., 1995; Tilly and Tilly 1995; Chun et al., 1995). Aurintricarboxylic acid has been shown to inhibit apoptotic cell death in various cell types induced by a variety of factors (Benchokroun et al., 1995).

BAPTA/AM [1,2,-bis(o-Aminophenoxy)ethane-N,N,N', N'-tetraacetic acid tetra (acetoxymethyl) ester] inhibits thapsigargin-induced apoptosis in rat thymocytes (Jiang et al., 1994). Caffeine has been shown to prevent apoptosis and cell cycle effects induced by camptothecin and topotecan in HL-60 cells (Traganos et al., 1993). Calpain inhibitor I inhibits apoptosis in thymocytes and metamyelocytes (Squier et al., 1994), while leupeptin, calpain inhibitor II and the E64 class of serine protease inhibitors have also been shown to inhibit activation-induced programmed cell death (Sarin et al., 1994). Cyclosporin A has been shown to prevent anti-IgM and ionomycin-induced apoptosis in BLB cell lines.

The general serine protease inhibitor 3,4-dichloroisocoumarin and the specific thiol reagent N-ethyl maleimide were shown to block apoptotic internucleosomal DNA cleavage in thymocytes without the involvement of endonucleases (Cain et al., 1994). The cysteine protease inhibitors E64 and leupeptin, the calpain selective inhibitor acetyl-leucyl-leucyl-normethional, and the serine protease inhibitors diisopropylfluorophosphate and phenylmethylsulfonyl fluoride were all shown to selectively block T-cell receptor-triggered programmed cell death in murine T-cell hybridoma and in activated peripheral T-cells (Sarin et al., 1993). Tetrodotoxin, nimodipine, verapamil, flunarizine and R56865 all protect bovine chromaffin cells from veratridine-induced cell death (Maroto et al., 1994).

Forskolin and insulin growth factor-1 (IGF-1) both have been shown to inhibit apoptosis in cerebellar granule cells, although by distinct mechanisms (Galli et al., 1995). The protein tyrosine kinase inhibitors genistein and herbimycin A have both been shown to prevent anti-CD3 monoclonal antibody-induced thymic apoptosis (Migita et al., 1994). Interleukin-6 (IL-6) inhibits constitutive, protein synthesis-independent apoptosis of murine B-cell hybridoma 7TD1 (Liu et al., 1994). The protein phosphatase inhibitors calyculin A and okadaic acid inhibit glucocorticoid-induced apoptosis in T-cell hybridomas (Gjertsen et al., 1994), and calyculin A is known to prevent γ-radiation induced apoptosis in Burkitt's lymphoma cell line BM 13674.

The protein kinase C activator phorbol-12-myristate-13-acetate inhibits apoptosis induced by the Fas antigen (Tepper et al., 1995). 1-Pyrrolidinecarbodithioic acid prevents apoptosis in human promyeolocytic leukemia HL-60 cells and in thymocytes (Bessho et al., 1994). The calcium-channel blockers nifedipine and nisoldipine, as well as the endonuclease inhibitor aurintricarboxylic acid have been shown to block apoptosis in cultured human endothelial cells (Escargueil-Blanc et al., 1997). Spermine has been shown to inhibit morphological apoptosis, and the antioxidant thioredoxin inhibits apoptosis in Jurkat T-cells and human PBL blasts (Sato et al., 1995). Additionally, the protease inhibitors $N^\alpha$-Tosyl-L-Phe chloromethyl ketone, $N^\alpha$-Tosyl-L-Lys chloromethyl ketone, and to a lesser extent $N^\alpha$-Tosyl-L-Arg methyl ester inhibit apoptosis in thymocytes (Bruno et al., 1992).

Additional apoptosis inhibitors contemplated for use in certain aspects of the present invention include, but are not limited to: (±)-verapamil hydrochloride; beta-lapachone; ALLM; ALLN; aphidicolin; aurintricarboxylic acid; caspase inhibitor I; caspase inhibitor II; caspase-1 inhibitor I; caspase-1 inhibitor II; caspase-1 inhibitor III; caspase-1 inhibitor IV; caspase-1 inhibitor V; caspase-2 inhibitor I; caspase-3 inhibitor I; caspase-3 inhibitor II; caspase-3 inhibitor III; caspase-4 inhibitor I; caspase-6 inhibitor I; caspase-6 inhibitor II; caspase-8 inhibitor I; caspase-9 inhibitor II; cathepsin B inhibitor I; compound 52; disulfiram; granzyme B inhibitor I; granzyme B inhibitor II; guanosine 3',5'-cyclic monophosphate; hemoglobin; JAK3 inhibitor II; phenylarsine oxide; phorbol-12,13-dibutyrate; PIPER; telomerase inhibitor V and ubiquitin aldehyde.

Antioxidants are useful in the present invention. Exemplary antioxidants include, but are not limited to: (+)-catechin hydrate ((+)-cyanidol-3(2R,3S)-2-(3,4-dihydroxyphenyl)-3,4-dihydro-1(2H)-benzopyran-3,5,7-triol); butylated hydroxytoluene (BHT; 2,(6)-di-tert-butyl-p-cresol); ellagic acid (4,4',5,5',6,6'-Hexahydroxydiphenic acid 2,6,2',6'-dilactone); ethyl gallate; lauryl gallate; methyl gallate; octyl gallate; 2',4',5'-trihydroxybutyrophenone; 2,4-di-tert-butylphenol; L-alpha-phosphatidylethanolamine (L-alpha-cephalin 1,2-diacyl-sn-glycero-3-phosphoethanolamine); carotene; coenzyme $Q_{10}$; coenzyme $Q_9$; 1,2-dihydro-6-ethoxy-2,2,4-trimethylquinoline; glutathione (γ-L-glutamyl-L-cysteinylglycine); hypotaurine (2-aminoethanesulfinic acid); N,N'-diphenyl-p-phenylenediamine; propyl gallate; (−)-1,4-dithio-L-threitol (L-DTT; Cleland Reagent; (2R,3R)-1,4-dimercapto-2,3-butanediol); (±)-6-hydroxy-2,5,7,8-tetra*mnethylchromane*-2-carboxylic acid; (+/−)-2-amino-6,7-dihydroxy-1,2,3,4-tetrahydro-naphthalene hydrobromide (6,7-ADTN hydrobromide); (+/−)-2-Dipropylamino-6,7-dihydroxy-1,2, 3,4-tetrahydronaphthalene hydrobromide (dipropyl-6,7-ADTN hydrobromide); (+)-α-tocopherol (vitamin E); (+)-γ-tocopherol; (+)-alpha-tocopherol acid succinate; (−)- gallocatechin ((2S,3R)-2-(3,4,5-trihydroxyphenyl)-3,4-dihydro-1(2H)-benzopyran-3,5,7-triol); 1,4-dithio-DL-threitol (DTT; Cleland Reagent racemic; (±)-threo-1,4-dimercapto-2,3-butanediol); 1,4-dithioerythritol (DTE; Cleland Reagent; erythro-2,3-dihydroxy-1,4-butanedithiol); erythro-1,4-dimercapto-2,3-butanediol); 2,2'-ethylidene-bis (4,6-di-tert-butylphenol); 2,2-methylenebis (6-tert-butyl-4-ethylphenol); 2,2-methylenebis(6-tert-butyl-4-methylphenol); 2,3-dimercaptopropanesulfonic acid; 2,6-di-tert-butyl-4-(dimethylaminomethyl)phenol; 2,6-di-tert-butyl-4-methylphenol (BHT, butylated hydroxytoluene, 2,6-di-tert-butyl-p-cresol); 2,6-di-tert-butyl-p-cresol (BHT; DBPC; 'butylhydroxytoluene'; 2,6-di-tert-butyl-4-methylphenol); 2-mercaptoethanol; 3,3,5,5-tetramethyl-[1,1-biphenyl]-4,4-diol; 3,4-dihydroxybenzylamine hydrobromide (DHBA hydrobromide); 3,4-dihydroxyphenylacetic acid (DOPAC); 3,9 bis(2,4 dicumylphenoxy)-2,4,8,10-tetraoxa-3,9-diphosphaspiro[5.5]undecane; 3-bromo-7-nitroindazole; 3-methoxy-4-hydroxyphenethylamine hydrochloride (3-methoxytyramine hydrochloride); 4,4-methylenebis(2,6-di-tert-butylphenol); 5-hydroxyindolacetic acid (5-HIAA); 6,6-dihydroxy-5,5-dimethoxy-[1,1-biphenyl]-3,3-dicarboxaldehyde; 6-hydroxy-2,5,7,8-tetramethylchroman-2-carboxylic acid; 6-hydroxydopa ±2,4,5-trihydroxyphenylalanine (6-hydroxy-DL-DOPA); 6-hydroxydopamine hydrobromide; β-apo-8'-carotenal (apocarotenal, 8'-apo-β,-caroten-8'-al); trans-β-carotene; DL-metanephrine hydrochloride 4-hydroxy-3-methoxy-alpha-(methylaminomethyl)benzenemethanol (DL-m-O-methylepinephrine); L-(+)-ergothioneine thioneine ((S)-alpha-carboxy-N,N,N-trimethyl-2-mercapto-1H-imidazole-4-ethanaminium); acacetin; all trans-retinol palmitate; anthrone; apoferritin; astaxanthin (3,3'-dihydroxy-beta,beta-carotene-4,4'-dione); benserazide hydrochloride; beta-carotene; caffeic acid phenethyl ester (CAPE); calcium thioglycolate trihydrate; catalase $H_2O_2$:$H_2$ oxidoreductase; ceruloplasmin; coenzyme $Q_2$ (ubiquinone-10; 2,3-dimethoxy-5-methyl-6-geranyl-1,4-benzoquinone); cysteamine (2-aminoethanethiol; 2-mercaptoethylamine); cysteamine hydrochloride (2-aminoethanethiol hydrochloride); 2-mercaptoethylamine hydrochloride); D-cysteine; deoxyepinephrine hydrochloride (epinine; N-methyldopamine); dipropyldopamine hydrobromide; ditetradecyl 3,3-thiodipropionate; DL-cysteine; dopamine hydrochloride (3-hydroxytyramine hydrochloride); ebselen; ebselen PZ5 1; gallic acid monohydrate (3,4,5-trihydroxybenzoic acid); glutaryl chloride; glycerol propoxylate; L(+)-ascorbic acid calcium salt dihydrate; L(+)-ascorbic acid iron(II) salt; L(+)-ascorbic acid magnesium salt; L(+)-ascorbic acid sodium salt; L(+)-ergothioneine inner salt (ergothioneine dihydrate); L-3,4-dihydroxyphenylalanine methyl ester hydrochloride (L-DOPA methyl ester hydrochloride); L-cysteine; metanephrine hydrochloride; N-acetyltryptamine (3-(2-N-acetylaminoethyl)indole); N-methyldopamine hydrochloride (epinine hydrochloride; deoxyepinephrine hydrochloride); nordihydroguaiaretic acid (NDGA; 1,4-bis (3,4-dihydroxyphenyl)-2,3-dimethylbutane); octadecadienoic acid; pentaerythritol tetrakis(3,5-di-tert-butyl-4-hydroxyhydrocinnamate); poly(1,2-dihydro-2,2,4-trimethylquinoline); poly(4-vinylphenol) [poly(4-hydroxystyrene)]; poly(epichlorohydrin-co-ethylene oxide-co-allyl glycidyl ether); poly(ethylene glycol)-block-poly (propylene glycol)-block-poly(ethylene glycol); poly (ethylene-co-1-butene); poly(ethylene-co-1-butene-co-1-hexene); poly(ethylene-co-methyl acrylate); poly(ethylene-co-methyl acrylate-co-acrylic acid); poly(ethylene-co-vinyl acetate-co-methacrylic acid); poly(oxymethylene); (+)-catechin; (+)-rutin hydrate; (±)-taxifolin; a-lipoic acid; p-nitroblue tetrazolium chloride; bilirubin; caffeic acid; carazostatin (*Streptomyces chromofuscus*); ceruloplasmin; copper diisopropylsalicylate; deferoxamine mesylate; DL-a-lipoic acid (dihydro-); DMNQ; DTPA dianhydride; ellagic acid, dihydrate; EUK-8, dihydrate; ferritin (Apo-); ferritin; glutathione monoethyl ester; L-ergothioneine; L-stepholidine (*Stephania intermedica*); luteolin; manoalide (*Luffariella variabilis*); MnTBAP; MnTMPyP; morin hydrate; N-acetyl-S-farnesyl-L-cysteine; NDGA (*Larrea divaricata*); propyl gallate; pyrrolostatin (*Streptomyces chrestomyceticus*); resveratrol; Trolox®; U-74389G; U-83836E and vitamin E succinate.

Exemplary protease inhibitors include, but are not limited to: $\alpha_1$-antichymotrypsin; $\alpha_1$-antitrypsin; e-amino-n-caproic acid; p-APMSF, hydrochloride; AEBSF, hydrochloride; ALLM; ALLN; amastatin (Streptomyces sp.); antipain, hydrochloride; antithrombin III; aprotinin; benzamidine, hydrochloride; bestatin; calpastatin; cathepsin B inhibitor I; cathepsin B inhibitor II; cathepsin inhibitor I; cathepsin inhibitor II; cathepsin inhibitor III; cathepsin L inhibitor II; cathepsin L inhibitor III; cathepsin/subtilisin inhibitor; chymostatin; chymotrypsin inhibitor I; chymotrypsin inhibitor II; cystatin; cytochalasin A; dansyl-pepstatin; diisopropylfluorophosphate; dipeptidylpeptidase IV inhibitor I; dipeptidylpeptidase IV inhibitor II; DL-2-mercaptomethyl-3-guanidinoethylthiopropanoic acid; ebelactone A (Streptomyces sp.); ebelactone B (Streptomyces sp.); EDTA; EGTA; elastase inhibitor; elastatinal; EST; NCO-700; PD 150606; pepstatin A; PPACK II, dihydrochloride; PPACK, dihydrochloride; subtilisin inhibitor I; subtilisin inhibitor II; subtilisin inhibitor III; subtilisin inhibitor IV; subtilisin inhibitor V; trypsin inhibitor and ZINCOV™ inhibitor.

Additionally, the use of viral genes such as crnA and EI B-19K, as well as provision of the proper extracellular matrix and integrins, as well as survival signals such as growth factors or cytokines or their receptors, are contemplated for use in inhibiting apoptosis. Further exemplary apoptosis inhibitors are listed below in Table 12.

TABLE 12

Exemplary Anti-Apoptosis Agents

| AGENTS | MODE OF ACTION |
| --- | --- |
| tyrosine kinases, both membrane-associated and cytoplasmic forms, such as Src family, Jak/Stats, Ros, Neu (also known as her2 or erbB-2; GenBank accession numbers M11730, X03363, U02326 and S57296), Fms, Ret, abl, Met serine/threonine kinases: Mos, Raf, protein kinase C, PIM-1 | perturb signal transduction |

TABLE 12-continued

Exemplary Anti-Apoptosis Agents

| AGENTS | MODE OF ACTION |
|---|---|
| growth factor and receptors: platelet derived growth factor (PDGF), insulin-like growth factor (IGF-1; GenBank accession number X04434 and M24599), insulin receptor substrate (IRS-1 (GenBank accession number S62539) and IRS-2 (Genbank accession number AB000732)), Erb family, epidermal growth factor (EGF), growth hormone, hepatocyte growth factor (HGF; GenBank accession number U11813) basic fibroblast growth factor (bFGF) | |
| small GTPases (G) proteins including the ras family, rab family, and Gs$_a$ (GenBank accession numbers X56009, X04409) | |
| receptor-type tyrosine phosphatase IA-2 | |
| cyclin-dependent protein kinases (cdk), classes A–E; members of the cyclin family such as cyclin D (GenBank accession numbers M64349 and M73554) | affect cell cycle |
| Myc family members including c-myc (GenBank accession numbers J00120, K01980, M23541, V00501, X00364), N-myc, and L-myc; Rel family members including NF-kappaB; c-Myb, Ap-1, fos, jun, insulinoma associated cDNA (IA-1), ErbB-1, PAX gene family | alter nuclear transcription |
| telomerase (human TERT GenBank accession numbers: AF018176 and AF015950) | lengthens telomeres of chromosomes |
| bcl-2 (GenBank accession numbers M14745, X06487) and family members including Bcl-xl, Mcl-l, Bak, A1, A20 | inhibit apoptosis |
| inhibitors of interleukin-1b-converting enzyme and family members | |
| viral proteins such as SV40 large T antigen (GenBank accession number J02400) and polyoma large T antigen, SV40 temperature sensitive large T antigen, adenovirus E1A and E1B, human papilomavirus E6 (GenBank accession numbers X67160, A06328, V01116, X03321) and E7 (GenBank accession numbers A06328, V01116, X03321) | pleiotropic activities |
| mutant tumor suppressor genes or proteins, including p53 (ovarian (GenBank accession numbers S53545, S62213, S62216); liver (GenBank accession numbers S62711, S62713, S62714, S67715, S72716); gastric (GenBank accession numbers S63157); colon (GenBank accession numbers S63610); bladder (GenBank accession numbers S85568, S85570, S85691); lung (GenBank accession numbers S41969, S41977); and glioma (GenBank accession numbers S85807, S85712, S85713)), retinoblastoma gene (Rb), Wilm's tumor (WT1), bax alpha, interleukin-1b-converting enzyme and family, MEN-1 gene (chromosome 11q13; GenBank accession number U93236), neurofibromatosis, type 1 (NF1), cdk inhibitor p16, colorectal cancer gene (DCC), familial adenomatosis polyposis gene (FAP), multiple tumor suppressor gene (MTS-1), BRCA1, and BRCA2 | failure to promote apoptosis |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods, and in the steps or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abraham, et al., *EMBO J.* 5:2523–2528, 1986.
Anderson, Choi, and BonDurant, "Survival of porcine inner cell masses in culture and after injection into blastocysts," *Theriogenology* 42:204–212, 1994.
Basha, et al., *Biol. Reprod.*, 20:431, 1979.
Baumbach, et al., *J. Biol. Chem.*, 261:12869, 1986.
Baumbach, et al., *Proc. Natl. Acad. Sci. USA.*, 81:2985, 1984.
Bazer and Roberts, *J. Exp. Zool.*, 228:373, 1983.
Bazer et al., *J. Anim. Sci.*, 41:1112, 1975.
Benchokroun, Couprie, and Larsen, "Aurintricarboxylic acid, a putative inhibitor of apoptosis, is a potent inhibitor of DNA topoisomerase II in vitro and in Chinese hamster fibrosarcoma cells," *Biochem. Pharmacol.* 49:305–313, 1995.
Berg, "Biological implications of electric field effects. V: Fusion of blastomeres and blastocysts of mouse embryos," *Bioelectrochem. Bioenerg.* 9:223, 1982.
Bessho, et al., "Pyrrolidine dithiocarbamate, a potent inhibitor of nuclear factor kappa B (NF-kappa B) activation, prevents apoptosis in human promyelocytic leukemia HL-60 cells and thymocytes," *Biochem. Pharmacol.* 48:1883–1889, 1994.

Borner, Myers, Sartor, Sei, Toko, Trepel, and Schneider, "Drug-induced apoptosis is not necessarily dependent on macromolecular synthesis or proliferation in the p53-negative human prostate cancer cell line PC-3," *Cancer Res.* 55:2122–2128, 1995.

Bruno, Del Bino, Lassota, Giaretti, and Darzynkiewicz, "Inhibitors of proteases prevent endonucleolysis accompanying apoptotic death of HL-60 leukemic cells and normal thymocytes," *Leukemia* 6:1113–1120, 1992.

Buhi et al., *J. Biol. Chem.*, 257:1712, 1982.

Cain, Inayat-Hussain, Kokileva, and Cohen, "DNA cleavage in rat liver nuclei activated by $Mg^{2+}$ or $Ca^{2+}+Mg^{2+}$ is inhibited by a variety of structurally unrelated inhibitors," Biochem. *Cell. Biol.* 72:631–638, 1994.

Campbell, McWhir, Ritchie, Wilmut, "Sheep cloned by nuclear transfer from a cultured cell line," *Nature*, 380:64, 1996.

Castro-Obregon and Covarrubias, "Role of retinoic acid and oxidative stress in embryonic stem cell death and neuronal differentiation," *FEBS Lett.* 381:93–97, 1996.

Cherny and Merei, "Evidence for pluripotency of bovine primordial germ cell-derived cell lines maintained in long-term culture," *Theriogenology 41:175, 1994.*

Chun, Eisenhauer, Kubo, and Hsueh, "Interleukin-1 beta suppresses apoptosis in rat ovarian follicles by increasing nitric oxide production," *Endocrinology* 136:3120–3127, 1995.

Collas, Balise, Hofmann, and Robl, "Electrical activation of mouse oocytes," *Theriogenology* 10 32:835, 1989.

Cossarizza, Franceschi, Monti, Salvioli, Bellesia, Rivabene, Biondo, Rainaldi, Tinari, and Malorni, "Protective effect of N-acetylcysteine in tumor necrosis factor-alpha-induced apoptosis in U937 cells: the role of mitochondria," *Exp. Cell Res.* 220:232–40, 1995.

Delhaise, Ectors, De Roover, Ectors and Dessy, "Nuclear transplantation using bovine primordial germ cells from male fetuses," *Reprod. Fertil. Dev.* 7:1217–1219, 1995.

Deveraux, Takahashi, Salvesen and Reed, "X-linked IAP is a direct inhibitor of cell-death proteases," *Nature* 388:300–304, 1997.

Doetschman et al., "The in vitro development of blastocyst-derived embryonic stem cell lines: Formation of visceral yolk sac, blood islands and myocardium", *J. Embryol. Exp. Morph.*, 20 87:27–45, 1985.

Doetschman, Williams, Maeda, "Establishment of hamster blastocyst-derived embryonic stem (ES) cells," *Dev. Biol.*, 127:224–227, 1988.

Dolci, Pesce and De Felici, "Combined action of stem cell factor, leukemia inhibitory factor, and cAMP on in vitro proliferation of mouse primordial germ cells," *Mol. Reprod. Dev.* 35:134–139, 1993.

Donovan, Stott, Cairns, Heasman and Wylie, "Migratory and postmigratory mouse primordial germ cells behave differently in culture," *Cell* 44:831–838, 1986.

Ducsay et al., *Biol. Reprod.*, 26:729, 1982.

Ducsay et al., *J. Anim. Sci.*, 59:1303, 1984.

Eddy, Clark, Gong, Fenderson, "Origin and migration of primordial germ cells in mammals," *Gamete Res.*, 4:333–362, 1981.

Escargueil-Blanc, Meilhac, Pieraggi, Arnal, Salvayre, and Negre-Salvayre, "Oxidized LDLs induce massive apoptosis of cultured human endothelial cells through a calcium-dependent pathway. Prevention by aurintricarboxylic acid," *Arterioscler. Thromb. Vasc. Biol.* 17:331–339, 1997.

Evans, Notarianni, Laurie, Moor, "Derivation and preliminary characterization of pluripotent cell lines from porcine and bovine blastocysts," *Theriogenology*, 33:125–128, 1990.

Feige, Negoescu, Keramidas, Souchelnitskey and Chambaz, "$\alpha_2$-Macroglobulin: A binding protein for transforming growth factor-$\beta$ and various cytokines," *Horm. Res.* 45:227–232, 1996.

Ferrari, Yan and Greene, "N-acetylcysteine (D- and L-stereoisomers) prevents apoptotic death of neuronal cells," *J. Neurosci.* 15:2857–2866, 1995.

Flaws, DeSanti, Tilly, Javid, Kugu, Johnson, Hirshfield, and Tilly, "Vasoactive intestinal peptide-mediated suppression of apoptosis in the ovary: potential mechanisms of action and evidence of a conserved antiatretogenic role through evolution," *Endocrinology* 136:4351–4359, 1995.

Fujio, Kunisada, Hirota, Yamauchitakihara and Kishimoto, "Signals through gp130 upregulate bcl-x gene expression via STAT1-binding cis-element in cardiac myocytes," *J. Clin. Invest.* 99:2898–2905, 1997.

Galli, Meucci, Scorziello, Werge, Calissano, and Schettini, "Apoptosis in cerebellar granule cells is blocked by high KCl, forskolin, and IGF-1 through distinct mechanisms of action: the involvement of intracellular calcium and RNA synthesis," *J. Neurosci.* 15:1172–1179, 1995.

Gerfen and Wheeler, "Isolation of embryonic cell-lines from porcine blastocysts," *Anim. Biotech.* 6:1–14, 1995.

Gjertsen, Cressey, Ruchaud, Houge, Lanotte, and Doskeland, "Multiple apoptotic death types triggered through activation of separate pathways by cAMP and inhibitors of protein phosphatases in one (IPC leukemia) cell line," *J. Cell Sci.* 107:3363–3377, 1994.

Graham, "The fusion of cells with one- and two-cell mouse embryos," *Wistar Inst. Symp. Monogr.* 9:19, 1969.

Hampton and Orrenius, "Dual regulation of caspase activity by hydrogen peroxide—implications for apoptosis," *FEBS Lett.* 414:552–556, 1997.

Hogan et al. "Manipulating the Mouse Embryo," Cold Spring Harbor. 1994.

Jiang, Chow, Nicotera, and Orrenius, "Intracellular Ca2+ signals activate apoptosis in thymocytes: studies using the Ca(2+)-ATPase inhibitor thapsigargin," *Exp. Cell Res.* 212:84–92, 1994.

Keefer, Stice, Mathews "Bovine inner cell mass cells as donor nuclei in the production of nuclear transfer embryos and calves," *Biol. Reprod*, 50:935–939, 1994.

Ketcham et al., *J. Biol. Chem.*, 260:5768, 1985.

Ketcham et al., *J. Biol. Chem.*, 264:557, 1989.

Labosky, Barlow and Hogan, "Mouse embryonic germ (EG) cell lines: Transmission through the germline and differences in the methylation imprint of insulin-like growth factor 2 receptor (Igf2r) gene compared with embryonic stem (ES) cell lines," *Development* 120:3197–3204, 1994.

Lavoir, Rumph, Moens, King, Plante, Johnson, Ding and Betteridge, "Development of bovine nuclear transfer embryos made with oogonia," *Biol. Reprod.* 56:194–199, 1997.

Leichthammer and Brem, "In vitro culture and cryopreservation of farm animals' primordial germ cells," *Theriogenology* 33:272, 1990.

Liu, Moor, Laurie and Notarianni, "Nuclear remodelling and early development in cryopreserved, porcine primordial germ cells following nuclear transfer into in vitro-matured oocytes," *Int. J. Dev. Biol.* 39:639–644, 1995.

Liu, Li, de Tribolet, Jaufeerally, Hamou, and Van Meir, "IL-6 stimulates growth and inhibits constitutive, protein synthesis-independent apoptosis of murine B-cell hybridoma 7TD1," *Cell. Immunol.* 155:428–435, 1994.

Lotem, Peled-Kamar, Groner and Sachs, "Cellular oxidative stress and the control of apoptosis by wild-type p53, cytotoxic compounds, and cytokines," *Proc. Natl. Acad Sci. USA* 93:9166–9171, 1996.

Machaty, Funahashi, Mayes, Day, Prather, "Effect of injecting calcium chloride into in vitro-matured porcine oocytes," *Biol. Reprod*, 54:316–322, 1996.

Malorni, Rivabene, Straface, Rainaldi, Monti, Salvioli, Cossarizza, and Franceschi, "3-Aminobenzamide protects cells from UV-B-induced apoptosis by acting on cytoskeleton and substrate adhesion," *Biochem. Biophys. Res. Commun.* 207:715–724, 1995.

Maroto, De la Fuente, Artalejo, Abad, Lopez, Garcia-Sancho,. and Garcia, "Effects of Ca2+ channel antagonists on chromaffin cell death and cytosolic Ca2+ oscillations induced by veratridine," *Eur. J. Pharmacol.* 270:331–339, 1994.

Martin, et al., *Cell* 63:203–211, 1990.

McGrath, and Solter, "Nuclear transplantation in the mouse embryo by microsurgery and cell fusion," *Science* 220:1300, 1983.

Migita, Eguchi, Kawabe, Mizokami, Tsukada, and Nagataki, "Prevention of anti-CD3 monoclonal antibody-induced thymic apoptosis by protein tyrosine kinase inhibitors," *J. Immunol.* 153:3457–3465, 1994.

Moens, Chesne, Delhaise, Delval, Ectors, Dessy, Renard and Heyman, "Assessment of nuclear totipotency of fetal bovine diploid germ cells by nuclear transfer," *Theriogenology* 46:871–880, 1996.

Moore and Piedrahita, "The effects of human leukemia inhibitory factor (HLIF) and culture medium on in vitro differentiation of cultured porcine inner cell mass (PICM)", *In Vitro Cellular & Developmental Biology Animal*, 33(1):62–71, 1997.

Murray, et al., *J. Biol. Chem.*, 264:4143, 1989.

Nagy et al., "Embryonic stem cells alone are able to support fetal development in the mouse," *Development*, 110:815–821, 1990.

Nakajima, Kashiwagi, Ohta, Furukawa, Hayashi, Kawashima, and Hayashi, "Nerve growth factor and epidermal growth factor rescue PC12 cells from programmed cell death induced by etoposide: distinct modes of protection against cell death by growth factors and a protein-synthesis inhibitor," *Neurosci. Lett.* 176:161–4, 1994.

Neimman, and Reichelt, "Manipulating early pig embryos," *J. Reprod Fertil.*, 48:75–94, 1993.

Notarianni, Laurie, Moor, Evans, "Maintenance and differentiation in culture of pluripotential embryonic cell lines from pig blastocysts," *J. Reprod Fertil.* 41 (suppl.):51–56, 1990.

Ohta, Kinoshita, Naito, Nozaki, Masutani, Tsuruo and Miyajima, "Requirement of the caspase-3/CPP32 protease cascade for apoptotic death following cytokine deprivation in hematopoietic cells," *J. Biol. Chem.* 272:23111–23116, 1997.

Onishi et al., "Production of chimeric pigs and the analysis of chimerism using mitochondrial deoxyribonucleic acid as a cell marker", *Biol. Reprod*, 51:1069–1075, 1994.

Ouhibi, Fulka, Kanka and Moor, "Nuclear transplantation of ectodermal cells in pig oocytes: ultrastructure and radiography," *Mol. Reprod. Dev.* 44:533–539, 1996.

Ozil, "The parthenogenetic development of rabbit oocytes after repetitive pulsatile electrical stimulation," *Development* 10: 117, 1990.

Pesce and De Felici, "Apoptosis in mouse primordial germ cells: A study by transmission and scanning electron microscope," *Anat. Embryol.* 189:435–440, 1994.

Pesce, Farrace, Piacentini, Dolci and De Felici, "Stem cell factor and leukemia inhibitory factor promote primordial germ cell survival by suppressing programmed cell death (apoptosis)," *Development* 118:1089–1094, 1993.

Piedrahita, Zhang, Hagaman, Clark, and Maeda, "Generation of mice carrying a mutant apolipoprotein E gene inactivated by gene targeting in mouse embryonic stem cells," *Proc. Natl. Acad. Sci. USA* 89:4471–4475, 1992.

Piedrahita, Anderson, BonDurant, "On the isolation of embryonic stem (ES) cells: Comparative behavior of murine, porcine, and ovine embryos," *Theriogenology*, 34:879–901, 1990.

Piedrahita, Moore, Oetama, Lee, Scales, Ramsoondar, Bazer, Ott, "Generation of transgenic porcine chimeras using primordial germ cell-derived colonies", *Biology of reproduction*, 58(5):1321–9, 1998.

Prather, Hoffman, Schoenbeck, Stumpf, Li, "Characterization of DNA synthesis during the 2-cell stage and the production of tetraploid chimeric pig embryos," *Mol. Reprod. Develop.*, 45:38–42, 1996.

Prather, and First, "Cloning of embryos," *J. Reprod. Fertil.* 40 (suppl):227, 1990.

Prather, Barnes, Sims, Robl, Eyestone, and First, "Nuclear transplantation in the bovine embryo: Assessment of donor nuclei and recipient oocyte stage," *Biol. Reprod.* 37:859–368, 1987.

Prather, Sims and First, "Nuclear transplantation in early pig embryos," *Biol. Reprod.* 41:414–418, 1989.

Renegar, et al., *Biol. Reprod.*, 27:1247, 1982.

Roberts and Bazer, *Bio Essays*, 1:8, 1984.

Sarin, Adams, and Henkart, "Protease inhibitors selectively block T cell receptor-triggered programmed cell death in a murine T cell hybridoma and activated peripheral T cells," *J. Exp. Med.* 178:1693–1700, 1993.

Sarin, Clerici, Blatt, Hendrix, Shearer, and Henkart, "Inhibition of activation-induced programmed cell death and restoration of defective immune responses of HIV+ donors by cysteine protease inhibitors," *J. Immunol.* 153:862–872, 1994.

Sato, Iwata, Nakamura, Hori, Mori, and Yodoi, "Thiol-mediated redox regulation of apoptosis. Possible roles of cellular thiols other than glutathione in T cell apoptosis," *J. Immunol.* 154:3194–3203, 1995.

Saunders et al.,*J. Biol. Chem.*, 260:3658, 1985.

Schlosnagle et al., *J. Biol. Chem.* 249:7574, 1974.

Sell, Baserga, and Rubin, "Insulin-like growth factor I (IGF-I) and the IGF-I receptor prevent etoposide-induced apoptosis," *Cancer Res.* 55:303–306, 1995.

Shim and Anderson, "Putative porcine embryonic germ cells maintained in long-term culture," *Biol. Reprod*, 52:136, 1995.

Shim, Gutierrez-Adan, Chen, BonDurant, Anderson, "Isolation of pluripotent stem cells from cultured porcine primordial germ cells," *Theriogenology*, 46:245, 1997.

Simmen et al., *Mol. Endocrinol.* 2:253, 1988.

Smith and Wilmut, "Influence of nuclear and cytoplasmic activity on the development in vivo of sheep embryos after nuclear transfer", *Biol. Reprod*, 40:1027–1032, 1989.

Smithies, "Altering genes in animals and humans," *In: Etiology of Human Disease at the DNA Level*, J. Lindsten and U. Pettersson, eds, Nobel Symposium 80, Raven Press, NY., pp. 221–231, 1991.

Squier, Miller, Malkinson, and Cohen, "Calpain activation in apoptosis," *J. Cell. Physiol.* 159:229–237, 1994.

Stack and Newport, "Developmentally regulated activation of apoptosis early in xenopus gastrulation results in cyclin A degradation during interphase of the cell cycle," *Development* 124:3185–3195, 1997.

Stefanis, Troy, Qi and Greene, "Inhibitors of trypsin-like serine proteases inhibit processing of the caspase Nedd-2 and protect PC12 cells and sympathetic neurons from death evoked by withdrawal of trophic support," *J. Neurochem.* 69:1425–1437, 1997.

Stewart, Gadi, Blatt, "Stem cells from primordial germ cells can reenter the germline," *Dev. Biol.*, 161:626–628, 1994.

Stewart, Vanek, Wagner, "Expression of foreign genes from retroviral vectors in mouse teratocarcinoma chimeras," *EMBO J.*, 4:3701–3709, 1985.

Stice, and Robl, "Nuclear reprogramming in nuclear transplant rabbit embryos," *Biol. Reprod.* 39:657–668, 1988.

Strelchenko, "Bovine pluripotent stem cells," *Theriogenology* 45:131–140, 1996.

Strojek, Reed, Hoover, Wagner, "A method for cultivating morphologically undifferentiated embryonic stem cells from porcine blastocysts," *Theriogenology* 33:901, 1990.

Tepper, Jayadev, Liu, Bielawska, Wolff, Yonehara, Hannun, and Seldin, "Role for ceramide as an endogenous mediator of Fas-induced cytotoxicity," *Proc. Natl. Acad. Sci. USA* 92:8443–8447, 1995.

Tewari and Dixit, "Fas- and TNF-induced apoptosis is inhibited by the poxvirus crmA gene product," *J. Biol. Chem.* 270:3255–3260, 1995.

Tilly, and Tilly, "Inhibitors of oxidative stress mimic the ability of follicle-stimulating hormone to suppress apoptosis in cultured rat ovarian follicles," *Endocrinology* 136:242–252, 1995.

Traganos, Kapuscinski, Gong, Ardelt, Darzynkiewicz, and Darzynkiewicz, "Caffeine prevents apoptosis and cell cycle effects induced by camptothecin or topotecan in HL-60 cells," *Cancer Res.* 53:4613–4618, 1993.

Tsunoda, Shioda, Onodera, Nakamura, and Uchida, "Differential sensitivity of mouse pronuclei and zygote cytoplasm to Hoescht staining and ultraviolet irradiation," *J. Reprod. Fertil.* 82:173, 1988.

Ueda, Jishage, Kamada, Uchida, Suzuki, "Production of mice entirely derived from embryonic stem (ES) cell with many passages by coculture of ES cells with cytochalasin B induced tetraploid embryos," *Experimental Animals*, 44(3):205–210, 1995.

Wakayama, Rodriguez, Perry, Yanagimachi and Mombaerts, "Mice cloned from embryonic stem cells," *Proc. Natl. Acad. Sci. USA* 96:14984–14989, 1999.

Ware and Axelrad, "Inherited resistance to N- and B-tropic murine leukemia viruses in vitro: Evidence that congenic mouse strains SIM and SIM.R differ at the Fv-1 locus," *Virology*, 50:339–348, 1972.

Watanabe, Shirayoshi, Koshimizu, Hashimoto, Yonehara, Eguchi, Tsujimot and Nakatsuji, "Gene transfection of mouse primordial germ cells in vitro and analysis of their survival and growth control," *Exp. Cell Res.* 230:76–83, 1997.

Westhusin, Levanduski, Scarborough, Looney, and Bondioli, "Utilization of fluorescent staining to identify enucleated demi-oocytes for utilization in bovine nuclear transfer," *Biol. Reprod.* (suppl.) 42:176, 1990.

Wheeler, "Development and validation of swine embryonic stem cells—A review", *Reprod. Fertil. Dev.*, 6:563–570, 1994.

Whittingham, "Parthenogenesis in mammals," in *Oxford reviews in reproductive biology* (ed. C. A. Finn), vol. 2, p. 205, Oxford University Press, England. 1980.

Willadsen, "Nuclear transplantation in sheep embryos," *Nature* 320:63, 1986.

Wilmut, Schuleke, McWhir, Kind and Campbell, "Viable offspring derived from fetal and adult mammalian cells," *Nature* 385:810–813, 1997.

What is claimed is:

1. A method of increasing the number of nuclear transfer competent cells within a mammalian cell population, comprising culturing said cell population in serum starvation media containing an amount of at least a first apoptosis inhibitor effective to increase the number of cells at the G0/G1 stage of the cell cycle within said cell population.

2. The method of claim 1, wherein said cell population comprises bovine or porcine fetal or embryonic fibroblasts or primordial germ cells.

3. The method of claim 1, wherein said serum starvation media comprise at least a first serine protease apoptosis inhibitor and at least a second antioxidant apoptosis inhibitor.

4. The method of claim 1, wherein said cell population is cultured in serum starvation media comprise between about 0.05% and about 2% serum.

5. The method of claim 4, wherein said cell population is cultured in serum starvation media comprising between about 0.1% and about 0.5% serum.

6. A method of growing fetal or embryonic fibroblasts or primordial germ cells, comprising growing a cell culture comprising fetal or embryonic fibroblasts or primordial germ cells on an effective density of feeder cells and in a biologically effective serum starvation medium comprising an amount of at least a first apoptosis inhibitor effective to increase the number of cells at the G0/G1 stage of the cell cycle when said cell culture is maintained for a time sufficient to obtain undifferentiated fetal or embryonic fibroblasts or primordial germ cells.

7. A method of nuclear transfer, comprising culturing a mammalian cell population containing cells at the G0/G1 stage of the cell cycle in serum starvation media comprising an amount of at least a first apopotosis inhibitor effective to increase the proportion of viable G0/G1 cells in said cell population; and fusing at least a first viable G0/G1 cells with an enucleated mammalian ovum.

8. The method of claim 7, wherein said cell population comprises somatic or primordial germ cells from an immature or adult mammal.

9. The method of claim 7, wherein said cell population comprises somatic or primordial germ cells from a mammalian fetus or embryo.

10. The method of claim 7, wherein said cell population comprises somatic cells from an immature or adult mammal, fetus or embryo.

11. The method of claim 7, wherein said cell population comprises primordial germ cells from an immature or adult mammal, fetus or embryo.

12. The method of claim 7, wherein said cell population comprises primordial germ cells.

13. The method of claim 7, wherein said cell population comprises fetal lung fibroblasts or embryonic fibroblast cells.

14. The method of claim 7, wherein said cell population comprises bovine or porcine cells.

15. The method of claim 7, wherein cells of said cell population are induced to enter the G0/G1 stage of the cell cycle by chemical treatment, nutrient deprivation, growth inhibition or manipulation of gene expression.

16. The method of claim 7, wherein said at least a first apoptosis inhibitor is a serine protease inhibitor or an antioxidant.

17. The method of claim 16, wherein said at least a first apoptosis inhibitor is a serine protease inhibitor.

18. The method of claim 17, wherein said at least a first apoptosis inhibitor is α2-macroglobulin (MAC), uteroferrin rose, 4-(2-aminoethyl) benzenesulfonyl hydrochloride (AEBSF), N-alpha-p-tosyl-L-lysine chloromethyl ketone (TLCK), 3,4-dichloroisocoumarin, a serpin or an E64 class serine protease inhibitor.

19. The method of claim 18, wherein said at least a first apoptosis inhibitor is α2-macroglobulin (MAC) and wherein said MAC is present substantially throughout the culture of said cell population.

20. The method of claim 16, wherein said at least a first apoptosis inhibitor is an antioxidant.

21. The method of claim 20, wherein said at least a first apoptosis inhibitor is N-acetylcysteine (NAC), butylated hydroxyanisole (BHA), cimetidine (CIM), N-t-butyl-α-phenylnitrone (BPN), glutathione (GSH) or thioredoxin.

22. The method of claim 21, wherein said at least a first apoptosis inhibitor is N-acetylcysteine (NAC) and wherein said NAC is present at or proximal to the initial stages of the culture of said cell population.

23. The method of claim 5, wherein said cell population is cultured in serum starvation media comprising at least a first and at least a second apoptosis inhibitor.

24. The method of claim 23, wherein said at least a first and at least a second apoptosis inhibitor are distinct serine protease inhibitors.

25. The method of claim 23, wherein said at least a first and at least a second apoptosis inhibitor are distinct antioxidants.

26. The method of claim 23, wherein said at least a first apoptosis inhibitor is a serine portease inhibitor and said at least a second apoptosis inhibitor is an antioxidant.

27. The method of claim 26, wherein said at least a first apoptosis inhibitor is α2-macroglobulin (MAC) and said at least a second apoptosis inhibitor is N-acetylcysteine (NAC).

28. The method of claim 23, wherein said cell population is cultured in serum starvation media comprising a plurality of apoptosis inhibitors.

29. The method of claim 7, wherein said cell population comprises viable G0/G1 cells that comprise at least a first exogenous DNA segment.

30. The method of claim 29, wherein said at least a first exogenous DNA segment comprises at least a first coding region that expresses a selected protein.

31. The method of claim 30, wherein said at least a first exogenous DNA segment comprises at least a first coding region that expresses an interleukin, collagen, interferon, blood protein, hormone, growth factor, cytokine, enzyme, receptor, binding protein, immune system protein, antigen, muscle protein or oncogene receptor protein.

32. The method of claim 30, wherein said at least a first exogenous DNA segment comprises at least a first and second coding region that each expresses a selected protein.

33. The method of claim 7, wherein said at least a first viable G0/G1 cell and said enucleated mammalian ovum are from the same mammalian species.

34. The method of claim 7, wherein said at least a first viable G0/G1 cell and said enucleated mammalian ovum are from distinct mammalian species.

35. The method of claim 7, wherein said at least a first viable G0/G1 cell or said enucleated mammalian ovum are from a lagomorph, bovine, porcine, ovine, equine, caprine, canine, feline, murine or primate species.

36. The method of claim 7, wherein a single viable G0/G1 cell from said cell population is fused with said enucleated mammalian ovum.

37. The method of claim 7, wherein said cell population is cultured in said serum starvation media for between about 3 and about 30 days.

38. The method of claim 37, wherein said cell population is cultured in said serun starvation media for between about 5 and about 14 days.

39. The method of claim 38, wherein said cell population is cultured in said serum starvation media for about 10 days.

40. A method of preparing mammalian cells at the G0/G1 stage of the cell cycle that contain a selected DNA segment, comprising:
a) culturing a mammalian cell population containing cells at the G0/G1 stage of the cell cycle in serum starvation media comprising an amount of at least a first apoptosis inhibitor effective to increase the proportion of viable G0/G1 cells in said cell population; and
b) introducing said DNA segment into the viable G0/G1 cells in said cell population.

41. The method of claim 40, wherein said cell population comprises bovine or porcine fetal or embryonic fibroblasts or primordial germ cells.

42. The method of claim 40, wherein said serum starvation media comprises at least a first serine protease apoptosis inhibitor and at least a second antioxidant apoptosis inhibitor.

43. The method of claim 40, wherein said at least a first apoptosis inhibitor is α2-macroglobulin (MAC), N-acetylcysteine (NAC), butylated hydroxyanisole (BHA), cimetidine (CIM), N-t-butyl-α-phenylnitrone (BPN) or glutathione (GSH).

44. A method of nuclear transfer, comprising culturing a cell population containing bovine or porcine fetal or embryonic fibroblasts or primordial germ cells at the G0/G1 stage of the cell cycle in serum starvation media comprising an amount of at least a first apoptosis inhibitor effective to increase the proportion of viable G0/G1 cells in said cell population; and fusing at least a first viable G0/G1 cell from the cultured cell population with an enucleated bovine or porcine ovum, thereby achieving nuclear transfer.

45. The method of claim 44, wherein said media comprises at least a first serine protease apoptosis inhibitor and at least a second antioxidant apoptosis inhibitor.

46. The method of claim 44, wherein said at least a first apoptosis inhibitor is α2-macroglobulin (MAC), N-acetylcysteine (NAC), butylated hydroxyanisole (BHA), cimetidine (CIM), N-t-butyl-α-phenylnitrone (BPN) or glutathione (GSH).

47. A method of nuclear transfer, comprising culturing a mammalian cell population containing cells at the G0/G1 stage of the cell cycle in serum starvation media comprising an amount of the apoptosis inhibitor α2-macroglobulin (MAC) effective to increase the proportion of viable G0/G1 cells in said cell population when present substantially throughout the culture of said cell population; and fusing at least a first viable G0/G1 cell from the cultured cell population with an enucleated mammalian ovum, thereby achieving nuclear transfer.

48. The method of claim 47, wherein said cell population comprises bovine or porcine fetal or embryonic fibroblasts or primordial germ cells.

49. A method of nuclear transfer, comprising culturing a mammalian cell population containing cells at the G0/G1 stage of the cell cycle in serum starvation media comprising an apoptosis inhibitor selected from the group consisting of N-acetylcysteine (NAC), butylated hydroxyanisole (BHA), cimetidine (CIM), N-t-butyl-α-phenylnitrone (BPN) and glutathione (GSH) in an amount effective to increase the proportion of viable G0/G1 cells in said cell population; and fusing at least a first viable G0/G1 cell from the cultured cell population with an enucleated mammalian ovum, thereby achieving nuclear transfer.

50. The method of claim 49, wherein said cell population comprises bovine or porcine fetal or embryonic fibroblasts or primordial germ cells.

51. A method of nuclear transfer, comprising culturing a mammalian cell population containing cells at the G0/G1 stage of the cell cycle in serum starvation media comprising an amount of the apoptosis inhibitor N-acetylcysteine (NAC) effective to increase the proportion of viable G0/G1 cells in said cell population when present at the initial stages of the culture of said cell population; and fusing at least a first viable G0/G1 cell from the cultured cell population with an enucleated mammalian ovum, thereby achieving nuclear transfer.

52. The method of claim 51, wherein said cell population comprises bovine or porcine fetal or embryonic fibroblasts or primordial germ cells.

53. A method of nuclear transfer, comprising culturing a mammalian cell population containing cells at the G0/G1 stage of the cell cycle in serum starvation media comprising at least a first serine protease apoptosis inhibitor and at least a second antioxidant apoptosis inhibitor in an amount effective to increase the proportion of viable G0/G1 cells in said cell population; and fusing at least a first viable G0/G1 cell from the cultured cell population with an enucleated mammalian ovum, thereby achieving nuclear transfer.

54. The method of claim 53, wherein said cell population comprises bovine or porcine fetal or embryonic fibroblasts or primordial germ cells.

55. A method of nuclear transfer, comprising culturing a mammalian cell population containing cells at the G0/G1 stage of the cell cycle in serum starvation media comprising an amount of at least a first serine protease apoptosis inhibitor other than a2-macroglobulin effective to increase the proportion of viable G0/G1 cells in said cell population; and fusing at least a first viable G0/G1 cell with an enucleated mammalian ovum.

56. A method of nuclear transfer, comprising culturing a mammalian cell population containing cells at the G0/G1 stage of the cell cycle in serum starvation media comprising an amount of at least a first antioxidant apoptosis inhibitor other than thioredoxin in an amount effective to increase the proportion of viable G0/G1 cells in said cell population; and fusing at least a first viable G0/G1 cell with an enucleated mammalian ovum.

57. A method of nuclear transfer, comprising culturing a mammalian cell population containing cells at the G0/G1 stage of the cell cycle in serum starvation media comprising an amount of at least a first apoptosis inhibitor other than α2-macroglobulin, thioredoxin or uteroferrin in an amount effective to increase the proportion of viable G0/G1 cells in said cell population; and fusing at least a first viable G0/G1 cell with an enucleated mammalian ovum.

58. A method of cloning a mammal from somatic or primordial germ cells, comprising:
 (a) culturing a population of mammalian somatic or primordial germ cells containing cells at the G0/G1 stage of the cell cycle in serum starvation media comprising an effective amount of at least a first apoptosis inhibitor for a period of time suitable to increase the proportion of viable G0/G1 cells in said population; and
 (b) generating a viable cloned mammal from at least a first of said viable G0/G1 cells.

59. A method of producing a transgenic mammal, comprising:
 (a) culturing a population of mammalian somatic or primordial germ cells containing cells at the G0/G1 stage of the cell cycle in serum starvation media comprising an effective amount of at least a first apoptosis inhibitor for a period of time suitable to increase the proportion of viable G0/G1 cells in said population;
 (b) introducing a selected DNA segment into viable G0/G1 cells of said cell population to produce viable transgenic G0/G1 cells; and
 (c) generating a transgenic mammal from at least a first of said viable transgenic G0/G1 cells.

60. A method of producing a mammalian cell line from a somatic mammalian cell, comprising:
 (a) culturing a population of said somatic cells containing cells at the G0/G1 stage of the cell cycle in serum starvation media comprising an effective amount of at least a first apoptosis inhibitor for a period of time suitable to increase the proportion of viable G0/G1 somatic cells in said population;
 (b) fusing at least a first of said viable G0/G1 somatic cells with an enucleated mammalian ovum;
 (c) culturing the fused cell/ovum in embryo media for a period of time effective to reach the morula/blastocyst stage of development; and
 (d) culturing the morula/blastocyst in complete media for period of time effective to allow the development of a mammalian cell line.

* * * * *